United States Patent
Armel et al.

(10) Patent No.: US 11,766,044 B2
(45) Date of Patent: *Sep. 26, 2023

(54) METHOD FOR CONTROLLING PPO RESISTANT WEEDS

(71) Applicant: BASF SE, Ludwigshafen (DE)

(72) Inventors: Gregory Armel, Research Triangle Park, NC (US); Cyrill Zagar, Research Triangle Park, NC (US); Andreas Landes, Limburgerhof (DE); Tobias Seiser, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/862,942

(22) Filed: Jul. 12, 2022

(65) Prior Publication Data

US 2022/0361495 A1    Nov. 17, 2022

Related U.S. Application Data

(63) Continuation of application No. 17/091,111, filed on Nov. 6, 2020, now Pat. No. 11,419,337, which is a continuation of application No. 16/321,237, filed as application No. PCT/EP2017/068784 on Jul. 25, 2017, now Pat. No. 10,863,743.

(60) Provisional application No. 62/368,199, filed on Jul. 29, 2016.

(30) Foreign Application Priority Data

Dec. 20, 2016 (EP) .................................. 16205236

(51) Int. Cl.
*A01N 43/54* (2006.01)
*A01N 41/10* (2006.01)
*C07D 239/54* (2006.01)
*C07D 401/12* (2006.01)

(52) U.S. Cl.
CPC .......... *A01N 43/54* (2013.01); *C07D 239/54* (2013.01); *C07D 401/12* (2013.01); *A01N 41/10* (2013.01)

(58) Field of Classification Search
None
See application file for complete search history.

(56) References Cited

U.S. PATENT DOCUMENTS

| | | | |
|---|---|---|---|
| 6,537,948 B1 | 3/2003 | Tohyama et al. |
| 10,378,023 B2 | 8/2019 | Evdokimov et al. |
| 10,563,220 B2 | 2/2020 | Ellis et al. |
| 10,863,743 B2 | 12/2020 | Armel et al. |
| 10,982,227 B2 | 4/2021 | Aponte et al. |
| 2009/0233796 A1 | 9/2009 | North |
| 2010/0048399 A1 | 2/2010 | Hacker et al. |
| 2013/0102463 A1 | 4/2013 | Ehrhardt et al. |
| 2021/0051959 A1 | 2/2021 | Armel et al. |

FOREIGN PATENT DOCUMENTS

| | | |
|---|---|---|
| EP | 1122244 B1 | 9/2004 |
| EP | 1397958 B1 | 1/2007 |
| EP | 1470753 B1 | 6/2007 |
| WO | WO-2006/061562 A1 | 6/2006 |
| WO | WO-2007/014758 A1 | 2/2007 |
| WO | WO-2007/083090 A2 | 7/2007 |
| WO | WO-2011/137088 A1 | 11/2011 |
| WO | WO-2016/113334 A1 | 7/2016 |
| WO | WO-2016/116531 A1 | 7/2016 |
| WO | WO-2016/120116 A1 | 8/2016 |
| WO | WO-2016/203377 A1 | 12/2016 |
| WO | WO-2017/007873 A1 | 1/2017 |
| WO | WO-2017/009054 A1 | 1/2017 |
| WO | WO-2017/009056 A1 | 1/2017 |
| WO | WO-2017/009060 A1 | 1/2017 |
| WO | WO-2017/009061 A1 | 1/2017 |
| WO | WO-2017/009088 A1 | 1/2017 |
| WO | WO-2017/009089 A1 | 1/2017 |
| WO | WO-2017/009090 A1 | 1/2017 |
| WO | WO-2017/009092 A1 | 1/2017 |
| WO | WO-2017/009095 A1 | 1/2017 |
| WO | WO-2017/009124 A1 | 1/2017 |
| WO | WO-2017/009134 A1 | 1/2017 |
| WO | WO-2017/009137 A1 | 1/2017 |
| WO | WO-2017/009138 A1 | 1/2017 |
| WO | WO-2017/009139 A1 | 1/2017 |
| WO | WO-2017/009140 A1 | 1/2017 |
| WO | WO-2017/009142 A1 | 1/2017 |
| WO | WO-2017/009143 A1 | 1/2017 |
| WO | WO-2017/009144 A1 | 1/2017 |
| WO | WO-2017/009145 A1 | 1/2017 |
| WO | WO-2017/009146 A1 | 1/2017 |
| WO | WO-2017/009147 A1 | 1/2017 |
| WO | WO-2017/009148 A1 | 1/2017 |

(Continued)

OTHER PUBLICATIONS

Anonymous, "Syn-523 (S-3100)", Jan. 14, 2012, XP055350912, retrieved from the internet (http://agroip_blogspotcom/2012/01/syn-523.html).

(Continued)

*Primary Examiner* — Alton N Pryor
(74) *Attorney, Agent, or Firm* — MARSHALL, GERSTEIN & BORUN LLP

(57) ABSTRACT

A method for controlling PPO resistant weeds, wherein compounds of formula (I)

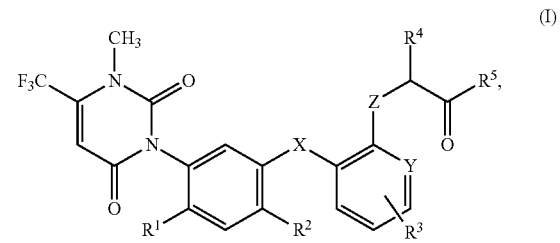

wherein the variables are defined as given in the description and claims;
are applied to the PPO inhibitor herbicide resistant weed, parts of it or its propagation material.

4 Claims, No Drawings

(56) References Cited

FOREIGN PATENT DOCUMENTS

| WO | WO-2017/021430 A1 | 2/2017 |
| WO | WO-2017/198859 A1 | 11/2017 |
| WO | WO-2017/202768 A1 | 11/2017 |
| WO | WO-2017/202774 A1 | 11/2017 |
| WO | WO-2018/015180 A1 | 1/2018 |
| WO | WO-2018/019552 A1 | 2/2018 |
| WO | WO-2018/019554 A1 | 2/2018 |
| WO | WO-2018/019555 A1 | 2/2018 |
| WO | WO-2018/019574 A1 | 2/2018 |
| WO | WO-2018/019721 A1 | 2/2018 |
| WO | WO-2018/019755 A1 | 2/2018 |
| WO | WO-2018/019758 A1 | 2/2018 |
| WO | WO-2018/019765 A1 | 2/2018 |
| WO | WO-2018/019767 A1 | 2/2018 |
| WO | WO-2018/019770 A1 | 2/2018 |
| WO | WO-2018/019845 A1 | 2/2018 |
| WO | WO-2018/019860 A1 | 2/2018 |

OTHER PUBLICATIONS

Beckie et al., "Herbicide cross resistance in weeds", Crop Protection, 2012, p. 15-28, vol. 35.

Bond et al., "Managing PPO-resistant Palmer Amaranth in Mississippi Soybean", Mar. 25, 2016, pp. 1-4, KP055349946, retrieved from the internet (http://www.mississippi-crops.com/2016/03/25/managing-ppo-resistant-palmer-amaranth-in-mississippi-soybean/).

Dayan et al., "Evolution of resistance to phytoene desaturase and protoporphyrinogen oxidase inhibitors—state of knowledge", Pesticide Manag. Sci., 2014, p. 1358-1366, vol. 70.

European Search Report for EP Patent Application No. 16205236.9, dated Mar. 13, 2017, 5 pages.

Final Office Action dated Aug. 1, 2019 in U.S. Appl. No. 16/127,936, filed Sep. 11, 2018.

International Search Report dated Aug. 21, 2017 for PCT/EP2017/068784.

Office action dated Feb. 5, 2019 in U.S. Appl. No. 16/127,936, filed Sep. 11, 2018.

Powles et al., Herbicide cross resistance and multiple resistance in plants, Herbie. Resist. Action Committee Monogr. 2 (1995). 1-19; obtained from Google Scholar at https://hracglobal.com/files/Herbicide-Cross-Resistance-and-Multiple-Resistance-in-Plants.pdf on Jul. 26, 2019.

Rousonelos et al., Characterization of a common ragweed (ambrosia artemisiifolia) population resistant to ALS- and PPO-inhibiting herbicides, Weed Science, 2012, p. 335-344, vol. 60.

METHOD FOR CONTROLLING PPO RESISTANT WEEDS

CROSS-REFERENCE TO RELATED APPLICATIONS

This application is a continuation of U.S. patent application Ser. No. 17/091,111 (filed Nov. 6, 2020), which is a continuation of U.S. patent application Ser. No. 16/321,237 (filed Jan. 28, 2019), which is incorporated herein by reference in its entirety and is a national stage of International Patent Application No. PCT/EP2017/068784 (filed Jul. 25, 2017), which claims the priority benefit of U.S. Provisional Application No. 62/368,199 (filed on Jul. 29, 2016) and EP Application No. 16205236.9 (filed on Dec. 20, 2016).

The invention relates to a method for controlling PPO resistant weeds, wherein at least one or more compounds of formula (I) are applied to the PPO inhibitor herbicide resistant weed, parts of it or its propagation material.

Herbicide resistant weeds present a serious problem for efficient weed control because such resistant weeds are increasingly widespread and thus weed control by the application of herbicides is no longer effective. In particular PPO resistant weeds are a huge problem to farmers.

Thus, there is a need for an effective and efficient method for the control of herbicide resistant weeds, in particular PPO resistant weeds.

In crop protection, it is desirable to increase the specificity and reliability of the action of active compounds. In particular, it is desirable for the crop protection product to control the harmful plants (weeds) effectively and, at the same time, to be tolerated by the useful plants (crops) in question.

Thus, there is a need for a novel method to effectively control herbicide resistant weeds, in particular PPO resistant weeds, which at the same time is tolerated by the useful plants (crops) in question.

Surprisingly it has been found that compounds of formula (I) provide an efficient control against PPO resistant weeds.

Some of the compounds of formula (I) and their herbicidal activities are disclosed in U.S. Pat. No. 6,537,948 and WO 2011/137088.

WO 2017/007873 discloses inter alia the control of glyphosate-resistant weeds by application of compositions comprising some compounds of formula (I) and glyphosate.

However, acceptable efficacy of compounds of formula (I) against PPO resistant weeds is unknown.

Accordingly, the present invention provides a method for controlling the growth of PPO resistant weeds, which comprises contacting such weeds, parts of it, its propagation material or its habitat with compounds of formula (I)

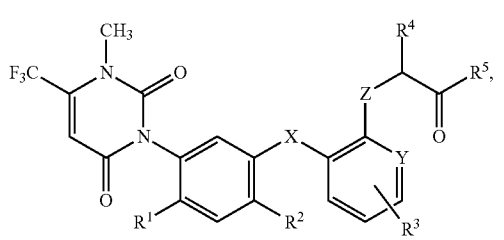

(I)

wherein
$R^1$ is H, F or Cl;
$R^2$ is F, Cl, Br, CN, C(O)NH$_2$ or C(S)NH;
$R^3$ is H, F, Cl, CH$_3$ or OCH$_3$;
$R^4$ is H, CN, CH$_3$, CF$_3$, OCH$_3$, OC$_2$H$_5$, SCH$_3$, SC$_2$H$_5$, (CO)OC$_2$H$_5$ or CH$_2$R$^6$,
 wherein $R^6$ is F, Cl, OCH$_3$, SCH$_3$, SC$_2$H$_5$, CH$_2$F, CH$_2$Br or CH$_2$OH;
$R^5$ is (C$_1$-C$_6$-alkyl)amino, (C$_1$-C$_6$-dialkyl)amino, (NH)OR$^7$, OH, OR$^8$ or SR$^8$,
 wherein $R^7$ is CH$_3$, C$_2$H$_5$ or phenyl; and
 $R^8$ is C$_1$-C$_6$-alkyl, C$_2$-C$_6$-alkenyl, C$_3$-C$_6$-alkynyl, C$_1$-C$_6$-haloalkyl, C$_1$-C$_6$-alkoxy-C$_1$-C$_6$-alkyl, C$_1$-C$_6$-alkoxy-C$_1$-C$_6$-alkoxy-C$_1$-C$_6$-alkyl, C$_2$-C$_6$-cyanoalkyl, C$_1$-C$_4$-alkoxy-carbonyl-C$_1$-C$_4$-alkyl, C$_1$-C$_4$-alkyl-carbonyl-amino, C$_1$-C$_6$-alkylsulfinyl-C$_1$-C$_6$-alkyl, C$_1$-C$_6$-alkyl-sulfonyl-C$_1$-C$_6$-alkyl, C$_1$-C$_6$-dialkoxy-C$_1$-C$_6$-alkyl, C$_1$-C$_6$-alkyl-carbonyloxy-C$_1$-C$_6$-alkyl, phenyl-carbonyl-C$_1$-C$_6$-alkyl, tri(C$_1$-C$_3$-alkyl)-silyl-C$_1$-C$_6$-alkyl, tri(C$_1$-C$_3$-alkyl)-silyl-C$_2$-C$_6$-alkenyl, tri(C$_1$-C$_3$-alkyl)-silyl-C$_2$-C$_6$-alkynyl, tri(C$_1$-C$_3$-alkyl)-silyl-C$_1$-C$_6$-alkoxy-C$_1$-C$_6$-alkyl, dimethylamino, tetrahydropyranyl, tetrahydrofuranyl-C$_1$-C$_3$-alkyl, phenyl-C$_1$-C$_6$-alkoxy-C$_1$-C$_6$-alkyl, phenyl-C$_1$-C$_3$-alkyl, pyridyl-C$_1$-C$_3$-alkyl, pyridyl or phenyl,
 wherein the pyridyl and phenyl rings independently of one another are substituted by one to five substituents selected from the group consisting of halogen, C$_1$-C$_3$-alkyl or C$_1$-C$_2$-haloalkyl;
 C$_3$-C$_6$-cycloalkyl or C$_3$-C$_6$-cycloalkyl-C$_1$-C$_4$-alkyl,
 wherein the cycloalkyl rings independently of one another are unsubstituted or substituted by one to five substituents selected from the group consisting of halogen, C$_1$-C$_3$-alkyl and C$_1$-C$_2$-haloalkyl,
X is O, S, S(O) or S(O)$_2$;
Y is N or CH; and
Z is O, S, S(O) or S(O)$_2$;
wherein the PPO resistant weeds are weeds, that are resistant to PPO-inhibiting herbicides except the compounds of formula (I).

The invention particularly relates to a method for controlling PPO resistant weeds in crops which comprises applying compounds of formula (I) according to the method of the present invention to crops, where said PPO herbicide resistant weeds occur or might occur.

The Invention furthermore relates to a method for controlling herbicide resistant weeds, which comprises allowing compounds of formula (I) according to the present Invention to act on plants, their habitat or on seed.

The present invention also provides a method for controlling PPO resistant weeds, wherein herbicidal compositions comprising at least one compound of formula (I) (component A) and at least one further compound selected from the herbicidal compounds B (component B) and/or safeners C (component C) are applied to such PPO resistant weeds, parts of them or their propagation material.

The present invention also provides a method for controlling PPO resistant weeds, wherein agrochemical compositions comprising at least one compounds of formula (I) and auxiliaries customary for formulating crop protection agents are applied to the PPO inhibitor herbicide resistant weed, parts of it or its propagation material.

The invention furthermore relates to the use of compounds of formula (I) or herbicidal composition comprising them for controlling PPO resistant weeds.

Accordingly, in another aspect of the invention there is provided use of compounds of formula (I) for controlling herbicide resistant weeds, in particular PPO resistant weeds.

The invention furthermore relates to a method for controlling undesirable vegetation, the method comprises applying compound of formula (I) according to the present invention to the undesirable plants. Application can be done before, during and/or after the emergence of the undesirable plants.

Further embodiments of the present invention can be found in the claims, the description and the examples. It is to be understood that the features mentioned above and those still to be illustrated below of the subject matter of the invention can be applied not only in the respective given combination but also in other combinations without leaving the scope of the invention.

As used herein, the terms "controlling" and "combating" are synonyms.

As used herein, the terms "undesirable vegetation", "harmful plants" and "Weeds" are synonyms.

As used herein, the terms "PPO inhibitor", "PPO inhibitor herbicide", "PPO-inhibiting herbicide", "protoporphyrinogen IX oxidase inhibitor herbicide", "protoporphyrinogen IX oxidase-inhibiting herbicide", "protoporphyrinogen oxidase inhibitor herbicide" and "protoporphyrinogen oxidase-inhibiting herbicide" are synonyms and refers to herbicide that inhibits enzyme protoporphyrinogen oxidase of a plant.

As used herein, the terms "PPO Inhibitor herbicide resistant weed", "PPO-inhibiting herbicide resistant weed", "PPO inhibitor resistant weed", "PPO resistant weed", "protoporphyrinogen IX oxidase inhibitor herbicide resistant weed", "protoporphyrinogen IX oxidase inhibiting herbicide resistant weed", "protoporphyrinogen oxidase inhibitor herbicide resistant weed", and "protoporphyrinogen oxidase inhibiting herbicide resistant weed" are synonyms and refer to a plant that, in relation to a treatment with an appropriate or over-appropriate rate of PPO-inhibiting herbicide application, has inherited, developed or acquired an ability
(1) to survive that treatment, if it is one that is lethal to (i.e. eradicates) the wild type weed; or
(2) to exhibit significant vegetative growth or thrive after that treatment, if it is one that suppresses growth of the wild-type weed.

Effective weed control is defined as at least 70% weed suppression or eradication from the crop, or as at least 70% weed plant phototoxicity, as determined 2 weeks after treatment.

Thus, PPO resistant weeds are weeds, which are not controlled by the application of PPO Inhibitors except the compound of formula (I), whereas the respective sensitive biotype is controlled at that use rate.

Here, "not controlled" means that in a visual rating the weed control (herbicidal effect) is <70% of weed suppression or eradication as determined 2 weeks after treatment; and "controlled" means that in a visual rating the weed control is >90% of weed suppression or eradication as determined 2 weeks after treatment.

Preferably, PPO resistant weeds are weeds, which are not controlled (i.e. in a visual rating the weed control is <70% of weed suppression or eradication as determined 2 weeks after treatment) by the application of PPO-inhibiting herbicides except the compound of formula (I).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin and flumioxazin.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from fomesafen and lactofen.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin, flumioxazin, fomesafen and lactofen.

Also preferably, PPO resistant weeds are weeds, which are not controlled (i.e. In a visual rating the weed control is <70% of weed suppression or eradication as determined 2 weeks after treatment) by the application of PPO-inhibiting herbicides selected from flumioxazin, fomesafen, lactofen, oxyfluorfen and sulfentrazone.

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin, flumioxazin, fomesafen, lactofen, oxyfluorfen and sulfentrazone.

Also preferably, PPO resistant weeds are weeds, which are not controlled (i.e. In a visual rating the weed control is <70% of weed suppression or eradication as determined 2 weeks after treatment) by the application of PPO-inhibiting herbicides selected from acifluorfen, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. In a visual rating the weed control is <70% of weed suppression or eradication as determined 2 weeks after treatment) by the application of PPO-inhibiting herbicides selected from acifluorfen, azafenidin, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide except the compound of formula (I).

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from azafenidin and flumioxazin.

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from fomesafen and lactofen.

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from azafenidin, flumioxazin, fomesafen and lactofen.

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from flumioxazin, fomesafen, lactofen, oxyfluorfen and sulfentrazone.

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from azafenidin, flumioxazin, fomesafen, lactofen, oxyfluorfen and sulfentrazone.

Also preferably, PPO resistant weeds are weeds, which are not controlled (i.e. In a visual rating the weed control is <70% of weed suppression or eradication as determined 2 weeks after treatment) by the application of at least one PPO-inhibiting herbicide selected from acifluorfen, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. In a visual rating the weed control is <70% of weed suppression or eradication as determined 2 weeks after treatment) by the application of at least one PPO-inhibiting herbicide selected from acifluorfen, azafenidin, carfentrazone, flumiclorac, flumioxazin, fomesafen, lactofen, oxadiazon, oxyfluorfen, pyraflufen and sulfentrazone.

Also preferably, PPO resistant weeds are weeds, which are not controlled (i.e. in a visual rating the weed control is <70% of weed suppression or eradication as determined 2 weeks after treatment) by the application of PPO-inhibiting herbicides except the compound of formula (I), whereas the respective sensitive biotype is controlled (i.e. In a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin and flumioxazin, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from fomesafen and lactofen, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from azafenidin, flumioxazin, fomesafen and lactofen, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from flumioxazin, fomesafen, lactofen, oxyfluorfen and sulfentrazone, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. In a visual rating the weed control is <70% of weed suppression or eradication as determined 2 weeks after treatment) by the application of PPO-inhibiting herbicides selected from azafenidin, flumioxazin, fomesafen, lactofen, oxyfluorfen and sulfentrazone, whereas the respective sensitive biotype is controlled (i.e. In a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from acifluorfen, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of PPO-inhibiting herbicides selected from acifluorfen, azafenidin, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide except the compound of formula (I), whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from azafenidin and flumioxazin, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from fomesafen and lactofen, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from azafenidin, flumioxazin, fomesafen and lactofen, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. In a visual rating the weed control is <70% of weed suppression or eradication as determined 2 weeks after treatment) by the application of at least one PPO-inhibiting herbicide selected from flumioxazin, fomesafen, lactofen, oxyfluorfen and sulfentrazone, whereas the respective sensitive biotype is controlled (i.e. In a visual rating the weed control is >90% of weed suppression or eradication as determined 2 weeks after treatment).

Also preferably, PPO resistant weeds are weeds, which are not controlled (i.e. in a visual rating the weed control is <70% of weed suppression or eradication as determined 2 weeks after treatment) by the application of at least one PPO-inhibiting herbicide selected from azafenidin, flumioxazin, fomesafen, lactofen, oxyfluorfen and sulfentrazone, whereas the respective sensitive biotype is controlled (i.e. in a visual rating the weed control is >90% of weed suppression or eradication as determined 2 weeks after treatment).

Also preferably, PPO resistant weeds are weeds, which are not controlled (i.e. In a visual rating the weed control is <70% of weed suppression or eradication as determined 2 weeks after treatment) by the application of at least one PPO-inhibiting herbicide selected from acifluorfen, carfentrazone, flumiclorac, flumioxazin, fomesafen, lactofen, oxadiazon, oxyfluorfen, pyraflufen and sulfentrazone, whereas the respective sensitive biotype is controlled (i.e. In a visual rating the weed control is >90% of weed suppression or eradication as determined 2 weeks after treatment).

Also preferably, PPO resistant weeds are weeds, which are not controlled (i.e. In a visual rating the weed control is <70% of weed suppression or eradication as determined 2 weeks after treatment) by the application of at least one PPO-inhibiting herbicide selected from acifluorfen, azafenidin, carfentrazone, flumiclorac, flumioxazin, fomesafen, lactofen, oxadiazon, oxyfluorfen, pyraflufen and sulfentrazone, whereas the respective sensitive biotype is controlled (i.e. In a visual rating the weed control is >90% of weed suppression or eradication as determined 2 weeks after treatment).

According to a specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to flumioxazin;
i.e. a method for controlling the growth of flumioxazin resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to fomesafen;
i.e. a method for controlling the growth of fomesafen resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to lactofen;
i.e. a method for controlling the growth of lactofen resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to oxyfluorfen;
i.e. a method for controlling the growth of oxyfluorfen resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to sulfentrazone;
i.e. a method for controlling the growth of sulfentrazone resistant weeds, which comprises contacting such weeds, parts of it, its propagation material or its habitat with compounds of formula (I).

According to another specific embodiment the present Invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from azafenidin and flumioxazin;
i.e. a method for controlling the growth of azafenidin and/or flumioxazin resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from fomesafen and lactofen;
i.e. a method for controlling the growth of fomesafen and/or lactofen resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from azafenidin, flumioxazin and fomesafen;
i.e. a method for controlling the growth of azafenidin, flumioxazin and/or fomesafen resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from azafenidin, flumioxazin and lactofen;
i.e. a method for controlling the growth of azafenidin, flumioxazin and/or lactofen resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from azafenidin, flumioxazin, fomesafen and lactofen;

i.e. a method for controlling the growth of azafenidin, flumioxazin fomesafen and/or lactofen resistant weeds, which comprises contacting such weeds, parts of it, its propagation material or its habitat with compounds of formula (I).

According to another specific embodiment the present Invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from flumioxazin, fomesafen, lactofen, oxyfluorfen and sulfentrazone;
i.e. a method for controlling the growth of flumioxazin, fomesafen, lactofen, oxyfluorfen and/or sulfentrazone resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from azafenidin, flumioxazin, fomesafen, lactofen, oxyfluorfen and sulfentrazone;
i.e. a method for controlling the growth of azafenidin, flumioxazin, fomesafen, lactofen, oxyfluorfen and/or sulfentrazone resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from acifluorfen, carfentrazone, flumiclorac, flumioxazin, fomesafen, lactofen, oxadiazon, oxyfluorfen, pyraflufen and sulfentrazone;
i.e. a method for controlling the growth of acifluorfen, carfentrazone, flumiclorac, flumioxazin, fomesafen, lactofen, oxadiazon, oxyfluorfen, pyraflufen and/or sulfentrazone resistant weeds, which comprises contacting such weeds, parts of it, its propagation material or its habitat with compounds of formula (I).

According to another specific embodiment the present invention provides a method for controlling the growth of PPO resistant weeds, which comprises contacting such weeds, parts of it, its propagation material or its habitat with compounds of formula (I), wherein the PPO resistant weeds are weeds, that are resistant to at least one PPO selected from acifluorfen, azafenidin, carfentrazone, flumiclorac, flumioxazin, fomesafen, lactofen, oxadiazon, oxyfluorfen, pyraflufen and sulfentrazone;
i.e. a method for controlling the growth of acifluorfen, azafenidin, carfentrazone, flumiclorac, flumioxazin, fomesafen, lactofen, oxadiazon, oxyfluorfen, pyraflufen and/or sulfentrazone resistant weeds, which comprises contacting such weeds, parts of it, its propagation material or its habitat with compounds of formula (I).

Also preferably, PPO resistant weeds are weeds, which are not controlled (i.e. In a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides except the compound of formula (I), whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from azafenidin and flumioxazin, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. In a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from fomesafen and lactofen, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from azafenidin, flumioxazin, fomesafen and lactofen, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from flumioxazin, fomesafen, lactofen, oxyfluorfen and sulfentrazone, whereas the respective sensitive biotype is controlled (i.e. In a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha, of PPO-inhibiting herbicides selected from azafenidin, flumioxazin, fomesafen, lactofen, oxyfluorfen and sulfentrazone, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from acifluorfen, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. In a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of PPO-inhibiting herbicides selected from acifluorfen, azafenidin, carfentrazone, flumiclorac, flumioxazin, fomesafen, lactofen, oxadiazon, oxyfluorfen, pyraflufen and sulfentrazone, whereas the respective sensitive biotype is controlled (i.e. In a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of at least one PPO-inhibiting herbicide except the compound of formula (I), whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of at least one PPO-inhibiting herbicide selected from azafenidin and flumioxazin, whereas the respective sensitive biotype is controlled (i.e. In a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of at least one PPO-inhibiting herbicide selected from fomesafen and lactofen, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. In a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of at least one PPO-inhibiting herbicide selected from azafenidin, flumioxazin, fomesafen and lactofen, whereas the respective sensitive biotype is controlled (i.e. In a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of at least one PPO-inhibiting herbicide selected from flumioxazin, fomesafen, lactofen, oxyfluorfen and sulfentrazone, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. in a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of at least one PPO-inhibiting herbicide selected from azafenidin, flumioxazin, fomesafen, lactofen, oxyfluorfen and sulfentrazone, whereas the respective sensitive biotype is controlled (i.e. in a visual rating the weed control is >90% of weed suppression or eradication as determined 2 weeks after treatment) at that use rate.

Also preferably, PPO resistant weeds are weeds, which are not controlled (i.e. In a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha,
of at least one PPO-inhibiting herbicide selected from acifluorfen, carfentrazone, flumiclorac, flumioxazin, fomesafen, lactofen, oxadiazon, oxyfluorfen, pyraflufen and sulfentrazone, whereas the respective sensitive biotype is controlled (i.e. In a visual rating the weed control is >90% of weed suppression or eradication as determined 2 weeks after treatment) at that use rate.

Also preferably, PPO resistant weeds are weeds, which are not controlled (i.e. In a visual rating the weed control is <70% of weed suppression or eradication as determined 2 weeks after treatment) by the application rate of
  200 g/ha or lower,
  particularly preferred 100 g/ha or lower,
  especially preferred 50 to 200 g/ha,
  more preferred 50 to 100 g/ha, of at least one PPO-inhibiting herbicide selected from acifluorfen, azafenidin, carfentrazone, flumiclorac, flumioxazin, fomesafen, lactofen, oxadiazon, oxyfluorfen, pyraflufen and sulfentrazone, whereas the respective sensitive biotype is controlled (i.e. in a visual rating the weed control is >90% of weed suppression or eradication as determined 2 weeks after treatment) at that use rate.

Also preferably PPO-resistant weeds are those classified as being "PPO resistant" and thus listed according to Anonymous: List of herbicide resistant weeds by herbicide mode of action—weeds resistant to PPO-inhibitors (URL: http://www.weedscience.org/summary/MOA.aspx).

Particularly preferred the PPO resistant weeds are selected from the group consisting of *Acalypha* ssp., *Amaranthus* ssp., *Ambrosia* ssp., *Avena* ssp., *Conyza* ssp., *Descurainia* ssp., *Euphorbia* ssp. and *Senecio* ssp.;
especially preferred *Amaranthus* ssp., *Ambrosia* ssp. and *Euphorbia* ssp.;
more preferred *Amaranthus* ssp. and *Ambrosia* ssp.

Also particularly preferred the PPO resistant weeds are selected from the group consisting of Asian copperleaf (*Acalypha australis*), smooth pigweed (*Amaranthus hybridus*), Palmer amaranth (*Amaranthus Palmeri*), redroot pigweed (*Amaranthus retroflexus*), tall/common waterhemp (*Amaranthus tuberculatus, Amaranthus rudis* or *Amaranthus tamariscinus*), common ragweed (*Ambrosia artemisiifolia* or *Ambrosia eliator*), wild oat (*Avena fatua*), fleabane (*Conyza ambigua*), marestall (*Conyza Canadensis*), flixweed (*Descurainia Sophia*), wild poinsettia (*Euphorbia heterophylla*) and eastern groundsel (*Senecio vernalis*);
especially preferred smooth pigweed (*Amaranthus hybridus*), Palmer amaranth (*Amaranthus Palmeri*), redroot pigweed (*Amaranthus retroflexus*), tall/common waterhemp (*Amaranthus tuberculatus, Amaranthus rudis* or *Amaranthus tamariscinus*), common ragweed (*Ambrosia aftemisiifolia* or *Ambrosia eliator*) and wild poinsettia (*Euphorbia heterophylla*);
more preferred tall/common waterhemp (*Amaranthus tuberculatus, Amaranthus rudis* or *Amaranthus tamariscinus*) and common ragweed (*Ambrosia artemisifolia* or *Ambrosia eliator*);

Most PPO resistant weeds, in particular the biotypes of *Amaranthus tuberculatus*, are resistant due to a codon deletion on the nuclear-encoded gene PPX2L that codes for the PPO enzyme which is dual-targeted to the mitochondria and the chloroplasts. This results in a loss of the glycine amino acid in position 210 (see e.g. B. G. Young et al, Characterization of PPO-Inhibitor-Resistant Waterhemp (*Amaranthus tuberculatus*) Response to Soil-Applied PPO-Inhibiting Herbicides, Weed Science 2015, 63, 511-521).

A second type of mutation, in particular in a resistant biotype of *Ambrosia artemisilfolia*, was Identified as a mutation that expressed a R98L change of the PPX2 enzyme (S. L. Rousonelos, R. M. Lee, M. S. Moreira, M. J. Van-Gessel, P. J. Tranel, Characterization of a Common Ragweed (*Ambrosia artemisiifolia*) Population Resistant to ALS- and PPO-Inhibiting Herbicides, Weed Science 60, 2012, 335-344).

Accordingly, preferably PPO-resistant weeds are weeds whose Protox enzyme is resistant to the application of PPO inhibitors due to a mutation that is expressed as a ΔG210 or R98L change of said Protox enzyme or equivalents to the PPX2L or PPX2 respectively, in particular that is expressed as a ΔG210 or R98L change of said Protox enzyme.

If the compounds of formula (I), the herbicidal compounds B and/or the safeners C as described herein are capable of forming geometrical isomers, for example E/Z isomers, it is possible to use both, the pure isomers and composition thereof, in the method according to the invention.

If the compounds of formula (I), the herbicidal compounds B and/or the safeners C as described herein have one or more centers of chirality and, as a consequence, are present as enantiomers or diastereomers, it is possible to use both, the pure enantiomers and diastereomers and their composition, in the method according to the invention.

If the compounds of formula (I), the herbicidal compounds B and/or the safeners C as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the Ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diethylammonium, diisopropylammonium, trimethylammonium, triethylammonium, tris (isopropyl)ammonium, heptylammonium, dodecylammonium, tetradecylammonium, tetramethylammonium, tetra-ethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyttrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Compounds of formula (I), herbicidal compounds B and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The preferred embodiments of the invention mentioned herein below have to be understood as being preferred either independently from each other or in combination with one another.

The organic moieties mentioned in the definition of the variables $R^1$ to $R^8$. are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix Cn-Cm denoting in each case the possible number of carbon atoms in the group. Examples of such meanings are:

- $C_1$-$C_2$-alkyl: for example $CH_3$ and $C_2H_5$;
- $C_1$-$C_3$-alkyl and also the $C_1$-$C_3$-alkyl moieties of tri($C_1$-$C_3$-alkyl)-silyl-$C_1$-$C_6$-alkyl, tri($C_1$-$C_3$-alkyl)-silyl-$C_1$-$C_6$-alkenyl, tri($C_1$-$C_3$-alkyl)-silyl-$C_2$-$C_6$-alkynyl, tri($C_1$-$C_3$-alkyl)-silyl-$C_1$-$C_6$-alkoxy-$C_1$-$C_6$-alkyl, tetrahydrofuranyl-$C_1$-$C_3$-alkyl, phenyl-$C_1$-$C_3$-alkyl, pyridyl-$C_1$-$C_3$-alkyl: for example $CH_3$, $C_2H_5$, n-propyl and $CH(CH_3)_2$;
- $C_1$-$C_4$-alkyl and also the $C_1$-$C_4$-alkyl moieties of $C_3$-$C_8$-cycloalkyl-$C_1$-$C_4$-alkyl, $C_1$-$C_4$-alkylcarbonylamino: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;
- $C_1$-$C_6$-alkyl and also the $C_1$-$C_6$-alkyl moieties of $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-alkoxycarbonyl-$C_1$-$C_6$-alkyl, $C_1$-$C_6$-alkylsulfinyl-$C_1$-$C_3$-alkyl, $C_1$-$C_6$-alkylsulfonyl-$C_1$-$C_6$-alkyl, $C_1$-$C_6$-dialkoxy-$C_1$-$C_6$-alkyl, $C_1$-$C_6$-alkyl-carbonyloxy-$C_1$-$C_6$-alkyl, phenyl-carbonyl-$C_1$-$C_6$-alkyl, tri($C_1$-$C_3$-alkyl)-silyl-$C_1$-$C_6$-alkyl, tri($C_1$-$C_3$-alkyl)-silyl-$C_1$-$C_6$-alkoxy-$C_1$-$C_6$-alkyl, phenyl-$C_1$-$C_6$-alkoxy-$C_1$-$C_4$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;
- $C_1$-$C_2$-haloalkyl: $C_1$-$C_2$-alkyl as mentioned above which is partially or fully substituted by fluorine, chlorine, bromine and/or Iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl;
- $C_1$-$C_4$-haloalkyl: $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyla $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;
- $C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;
- $C_3$-$C_6$-cycloalkyl and also the $C_3$-$C_6$-cycloalkyl moieties of $C_3$-$C_6$-cycloalkyl-$C_1$-$C_4$-alkyl: a monocyclic saturated hydrocarbon having 3 to 6 ring members, such as cyclopropyl, cyclobutyl, cyclopentyl and cyclohexyl;
- $C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;
- $C_2$-$C_6$-alkenyl and also the $C_2$-$C_6$-alkenyl moieties of tri($C_1$-$C_3$-alkyl)-silyl-$C_2$-$C_6$-alkenyl: $C_3$-$C_6$-alkenyl as mentioned above, and also ethenyl;
- $C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_1$-$C_6$-alkyny and also the $C_2$-$C_6$-alkynyl moieties of tri($C_1$-$C_3$-alkyl)-silyl-$C_2$-$C_6$-alkynyl: $C_3$-$C_6$-alkynyl as mentioned above and also ethynyl;

$C_1$-$C_6$-alkoxy and also the $C_1$-$C_6$-alkoxy moieties of $C_1$-$C_6$-alkoxy-$C_1$-$C_6$-alkyl, $C_1$-$C_6$-alkoxy-$C_1$-$C_6$-alkoxy-$C_1$-$C_6$-alkyl, $C_1$-$C_6$-alkoxycarbonyl-$C_1$-$C_6$-alkyl, tri($C_1$-$C_3$-alkyl)-silyl-$C_1$-$C_6$-alkoxy-$C_1$-$C_6$-alkyl, phenyl-$C_1$-$C_6$-alkoxy-$C_1$-$C_6$-alkyl, $C_1$-$C_6$-dialkoxy-$C_1$-$C_6$-alkyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

($C_1$-$C_6$-alkyl)amino: ($C_1$-$C_4$-alkylamino) as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_6$-alkyl)amino: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methylbutyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl)amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methyl-pentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino or N,N-dihexylamino;

$C_1$-$C_6$-alkylsulfinyl ($C_1$-$C_6$-Alkyl-S(=O)—) and also the $C_1$-$C_6$-alkylsulfinyl moieties of $C_1$-$C_6$-alkylsulfinyl-$C_1$-$C_6$-alkyl: for example methylsulfinyl, ethylsulfinyl, propylsulfinyl, 1-methylethylsulfinyl, butylsulfinyl, 1-methylpropylsulfinyl, 2-methylpropylsulfinyl, 1,1-di-methylethylsulfinyl, pentyisulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutyisulfinyl, 1,3-dimethylbutyl-sulfinyl, 2,2-dimethylbutyisulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$-$C_6$-alkylsulfonyl ($C_1$-$C_6$-alkyl-S(O)$_2$—) and also the $C_1$-$C_6$-alkylsulfonyl moieties of $C_1$-$C_6$-alkylsulfonyl-$C_1$-$C_6$-alkyl: for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethyl-butylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl.

According to a preferred embodiment of the invention preference is also given to those compounds of formula (I), wherein the variables, either independently of one another or in combination with one another, have the following meanings: Preferred are the compounds of formula (I), wherein $R^1$ is F.

Also preferred are the compounds of formula (I), wherein $R^2$ is Cl.

Also preferred are the compounds of formula (I), wherein $R^3$ is H.

Also preferred are the compounds of formula (I), wherein $R^4$ is H, $CH_3$ or $OCH_3$;
particularly preferred is H.

Also preferred are the compounds of formula (I), wherein $R^4$ is H, $OCH_3$ or $OC_2H_5$;
particularly preferred is H or $OCH_3$;
especially preferred is H.

Also preferred are the compounds of formula (I), wherein $R^5$ is $OR^8$, wherein $R^8$ is $C_1$-$C_6$-alkyl;
particularly preferred $OR^8$, wherein $R^8$ is $C_2H_5$.

Also preferred are the compounds of formula (I), wherein $R^5$ is OH or $OR^8$, wherein $R^8$ is $C_1$-$C_6$-alkyl;
particularly preferred OH or $OR^8$, wherein $R^a$ is $CH_3$ or $C_2H_5$;
especially preferred $OR^8$, wherein $R^8$ is $C_2H_5$.

Also preferred are the compounds of formula (I), wherein X is O.
Also preferred are the compounds of formula (I), wherein Y is N;
also preferred CH.
Also preferred are the compounds of formula (I), wherein Z is O.
Also preferred are the compounds of formula (I), wherein
$R^1$ is F;
$R^2$ is Cl;
$R^3$ is H;
$R^4$ is H, $OCH_3$ or $OC_2H_5$;
$R^5$ is OH or $OR^8$, wherein $R^8$ is $C_1$-$C_6$-alkyl;
X is O;
Y is N or CH; and
Z is O;
particularly preferred
$R^1$ is F;
$R^2$ is Cl;
$R^3$ is H;
$R^4$ is H or $OCH_3$;
$R^5$ is OH or $OR^8$, wherein $R^8$ is $CH_3$ or $C_2H_5$;
X is O;
Y is N or CH; and
Z is O;
especially preferred
$R^1$ is F;
$R^2$ is Cl;
$R^3$ is H;
$R^4$ is H;
$R^5$ is OH or $OR^8$, wherein $R^8$ is $CH_3$ or $C_2H_5$;
X is O;
Y is N or CH; and
Z is O;
more preferred
$R^1$ is F;
$R^2$ is Cl;
$R^3$ is H;
$R^4$ is H;
$R^5$ is OH or $OR^8$, wherein $R^8$ is $C_2H_5$;
X is O;
Y is N or CH; and
Z is O.
Also preferred are the compounds of formula (I), wherein
$R^1$ is F;
$R^2$ is Cl;
$R^3$ is H;
$R^4$ is H, $CH_3$ or $OCH_3$;
$R^5$ is OH or $OR^8$, wherein $R^8$ is $C_1$-$C_6$-alkyl;
X is O;
Y is N or CH; and
Z is O;
particularly preferred
$R^1$ is F;
$R^2$ is Cl;
$R^3$ is H;
$R^4$ is H, $CH_3$ or $OCH_3$;
$R^5$ is OH or $OR^8$, wherein $R^8$ is $CH_3$ or $C_2H_5$;
X is O;
Y is N or CH; and
Z is O.

In a particularly preferred embodiment, the compound of formula (I) is the compound (I).1 CAS

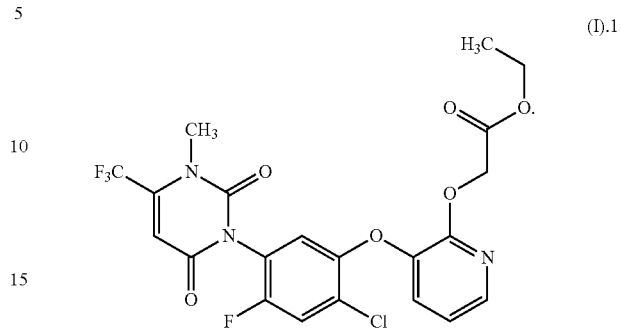

Accordingly, in a preferred embodiment of the present invention the method according to the present invention comprises the application of compound (I).1 to PPO resistant weeds.

In another particularly preferred embodiment, the compound of formula (I) is the compound (I).2:

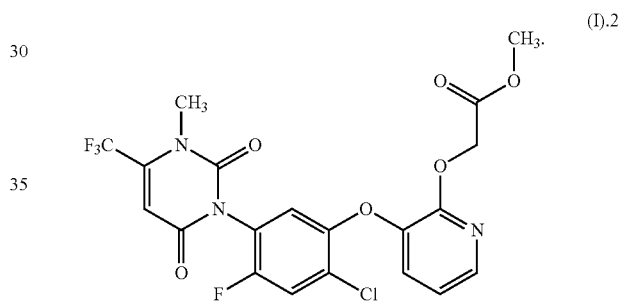

Accordingly, in a preferred embodiment of the present Invention the method according to the present Invention comprises the application of compound (I).2 to PPO resistant weeds.

In another particularly preferred embodiment, the compound of formula (I) is the compound (I).3:

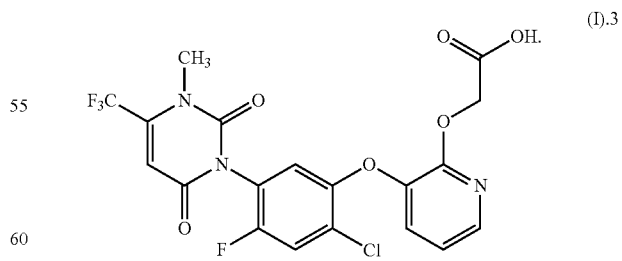

Accordingly, in a preferred embodiment of the present Invention the method according to the present Invention comprises the application of compound (I).3 to PPO resistant weeds.

In a particularly preferred embodiment the compound of formula I is the compound (I).4:

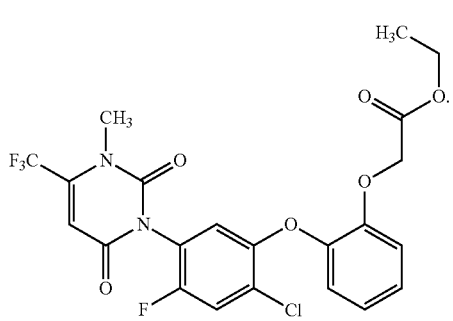

(I).4

Accordingly, in a preferred embodiment of the present invention the method according to the present invention comprises the application of compound (I).4 to PPO resistant weeds.

In another particularly preferred embodiment, the compound of formula (I) is the compound (I).5:

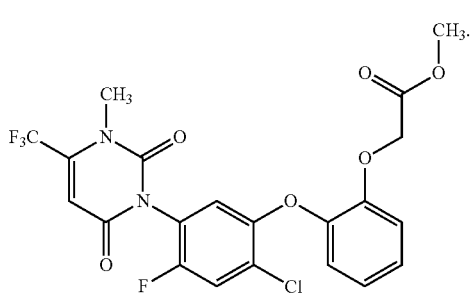

(I).5

Accordingly, in a preferred embodiment of the present Invention the method according to the present invention comprises the application of compound (I).5 to PPO resistant weeds.

In another particularly preferred embodiment, the compound of formula (I) is the compound (I).6:

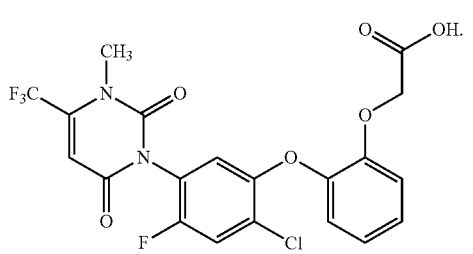

(I).6

Accordingly, in a preferred embodiment of the present Invention the method according to the present invention comprises the application of compound (I).6 to PPO resistant weeds.

In another preferred embodiment of the present invention the method according to the present invention comprises the application of at least one of the compounds selected from (I).1 and (I).4 to PPO resistant weeds [i.e. the compound of formula (I) is selected from at least one of the compounds of formulae (I).1 and (I.)4].

To broaden the spectrum of action and to achieve synergistic effects, the compounds of formula (I) may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithloates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrmidines, triketones, uracils, ureas.

It may furthermore be beneficial to apply the compounds of formula (I) alone or in combination with other herbicides, or else in the form of a mixture with other crop protection agents, for example together with agents for controlling pests or phytopathogenic fungi or bacteria.

Also of interest is the miscibility with mineral salt solutions, which are employed for treating nutritional and trace element deficiencies. Other additives such as non-phytotoxic oils and oil concentrates may also be added.

The present invention also relates to a method for controlling PPO herbicide resistant weeds, wherein a herbicidal composition of at least one compound of formula (I) and one or more further active compound as defined herein after is applied to the PPO herbicide resistant weeds.

In one embodiment of the present invention the method according to the present invention comprises the application of at least one compounds of formula (I) (compound A) and at least one further active compound selected from herbicides B, preferably herbicides B of class b1) to b15), and safeners C (compound C) to PPO resistant weeds.

In another embodiment of the present invention the method according to the present invention comprises the application of at least one compounds of formula (I) and at least one further active compound B (herbicide B) to PPO resistant weeds.

In one embodiment of the invention, the method according to the present invention comprises the application of a herbicidal composition comprising at least one, preferably exactly one compound of formula (I) and at least one further active compound selected from herbicides B, preferably herbicides B of class b1) to b15), and safeners C (compound C) to control PPO resistant weeds.

Accordingly, in a preferred embodiment of the present invention the method according to the present invention comprises the application of a herbicidal composition comprising at least one, preferably exactly one compound of formula (I) and at least one further active compound selected from herbicides B, preferably herbicides B of class b1) to b15), and safeners C (compound C) to PPO resistant weeds.

The further herbicidal compound B (component B) is preferably selected from the herbicides of class b1) to b15):

B) herbicides of class b1) to b15):
b1) lipid biosynthesis Inhibitors;
b2) acetolactate synthase Inhibitors (ALS Inhibitors);
b3) photosynthesis Inhibitors;
b4) protoporphyrinogen-IX oxidase Inhibitors (PPO Inhibitors) other than the compounds of formula (I);
b5) bleacher herbicides;
b6) enolpyruvyl shikimate 3-phosphate synthase Inhibitors (EPSP Inhibitors);
b7) glutamine synthetase Inhibitors;
b8) 7,8-dihydropteroate synthase Inhibitors (DHP Inhibitors);
b9) mitosis Inhibitors;
b10) Inhibitors of the synthesis of very long chain fatty acids (VLCFA Inhibitors);
b11) cellulose biosynthesis Inhibitors;
b12) decoupler herbicides;
b13) auxinic herbicides;
b14) auxin transport Inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;
including their agriculturally acceptable salts or derivatives.

In one embodiment of the invention, the method according to the present invention comprises the application of compositions containing at least one, preferably exactly one compound of formula (I) and as further active compound at least one inhibitor of the lipid biosynthesis (herbicide b1). These compounds inhibit lipid biosynthesis. Inhibition of the lipid biosynthesis can be affected either through inhibition of acetylCoA carboxylase (hereinafter-termed ACCase herbicides) or through a different mode of action (hereinafter termed non-ACCase herbicides). The ACCase herbicides belong to the group A of the HRAC classification system whereas the non-ACCase herbicides belong to the group N of the HRAC classification.

In another embodiment of the invention, the method according to the present invention comprises the application of compositions containing at least one, preferably exactly one compound of formula (I) and as further active compound at least one ALS inhibitor (herbicide b2). The herbicidal activity of these compounds is based on the Inhibition of acetolactate synthase and thus on the inhibition of the branched chain amino acid biosynthesis. These inhibitors belong to the group B of the HRAC classification system.

In another embodiment of the Invention, the method according to the present Invention comprises the application of compositions containing at least one, preferably exactly one compound of formula (I) and as further active compound at least one inhibitor of photosynthesis (herbicide b3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

In another embodiment of the Invention, the method according to the present Invention comprises the application of compositions containing at least one, preferably exactly one compound of formula (I) and as further active compound at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

In another embodiment of the invention, the method according to the present invention comprises the application of compositions containing at least one, preferably exactly one compound of formula (I) and as further active compound at least one bleacher-herbicide (herbicide b5). The herbicidal activity of these compounds is based on the inhibition of the carotenoid biosynthesis. These include compounds which inhibit carotenoid biosynthesis by inhibition of phytoene desaturase (so-called PDS inhibitors, group F1 of HRAC classification), compounds that inhibit the 4-hydroxyphenylpyruvate-dioxygenase (HPPD inhibitors, group F2 of HRAC classification), compounds that Inhibit DOXsynthase (group F4 of HRAC class) and compounds which inhibit carotenoid biosynthesis by an unknown mode of action (bleacher—unknown target, group F3 of H RAC classification).

In another embodiment of the Invention, the method according to the present Invention comprises the application of compositions containing at least one, preferably exactly one compound of formula (I) and as further active compound at least one EPSP synthase inhibitor (herbicide b6). The herbicidal activity of these compounds is based on the inhibition of enolpyruvyl shikimate 3-phosphate synthase, and thus on the inhibition of the amino acid biosynthesis in plants. These Inhibitors belong to the group G of the HRAC classification system.

In another embodiment of the invention, the method according to the present invention comprises the application of compositions containing at least one, preferably exactly one compound of formula (I) and as further active compound at least one glutamine synthetase inhibitor (herbicide b7). The herbicidal activity of these compounds is based on the inhibition of glutamine synthetase, and thus on the inhibition of the aminoacid biosynthesis in plants. These inhibitors belong to the group H of the HRAC classification system.

In another embodiment of the invention, the method according to the present invention comprises the application of compositions containing at least one, preferably exactly one compound of formula (I) and as further active compound at least one DHP synthase inhibitor (herbicide b8). The herbicidal activity of these compounds is based on the inhibition of 7, 8-dihydropteroate synthase. These Inhibitors belong to the group I of the HRAC classification system.

In another embodiment of the invention, the method according to the present invention comprises the application of compositions containing at least one, preferably exactly one compound of formula (I) and as further active compound at least one mitosis inhibitor (herbicide b9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

In another embodiment of the invention, the method according to the present invention comprises the application of compositions containing at least one, preferably exactly one compound of formula (I) and as further active compound at least one VLCFA Inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

In another embodiment of the Invention, the method according to the present Invention comprises the application of compositions containing at least one, preferably exactly one compound of formula (I) and as further active compound at least one cellulose biosynthesis inhibitor (herbicide b11). The herbicidal activity of these compounds is based on the inhibition of the biosynthesis of cellulose and thus on the Inhibition of the synthesis of cell walls in plants. These inhibitors belong to the group L of the HRAC classification system.

In another embodiment of the invention, the method according to the present invention comprises the application of compositions containing at least one, preferably exactly one compound of formula (I) and as further active compound at least one decoupler herbicide (herbicide b12). The herbicidal activity of these compounds is based on the disruption of the cell membrane. These inhibitors belong to the group M of the HRAC classification system.

In another embodiment of the Invention, the method according to the present Invention comprises the application of compositions containing at least one, preferably exactly one compound of formula (I) and as further active compound at least one auxinic herbicide (herbicide b13). These include compounds that mimic auxins, i.e. plant hormones, and affect the growth of the plants. These compounds belong to the group O of the HRAC classification system.

In another embodiment of the invention, the method according to the present invention comprises the application of compositions containing at least one, preferably exactly one compound of formula (I) and as further active compound at least one auxin transport Inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www-.plantprotection.org/hrac/MOA.html).

Preference is given to those methods according to the present invention comprising the application of composition comprising at least one herbicide B selected from herbicides of class b1, b2, b3, b4, b5, b6, b7, b10, b13, b14 and b15.

Specific preference is given to those methods according to the present invention comprising the application of compositions comprising at least one herbicide B selected from the herbicides of class b2, b4, b6, b7, b9, b10 and b13.

Particular preference is given to those methods according to the present Invention comprising the application of compositions comprising at least one herbicide B selected from the herbicides of class b4, b6, b7 and b13.

Examples of herbicides B which can be used in combination with the compound of formula (I) according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim,
4-(4'-Chloro-4-cyclopropyl-2-fluoro[1,1'-biphenyl]-3-yl)-5-hydroxy-2,2,6,6-tetramethyl-2H-pyran-3(6H)-one (CAS 1312337-72-6); 4-(2,4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2-fluoro[1,1'-biphenyl]-3-yl)-5-hydroxy-2,2,6,6-tetramethyl-2H-pyran-3(6H)-one (CAS 1033757-93-5); 4-(2,4'-Dichloro-4-ethyl[1,1'-biphenyl]-3-yl)-2,2,6,6-tetramethyl-2H-pyran-3,5 (4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(7,4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vemolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam,
pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6- dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy] benzenemethanamine (CAS 420138-01-8).
sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;
among these, a preferred embodiment of the invention relates to those compositions comprising at least one imidazolinone herbicide;

b3) from the group of the photosynthesis inhibitors:
amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methyithiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, loxynil and its salts and esters, uraciles such as bromacil, lenacil and terbacil, and bentazone and bentazone-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlorphtalim, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoro-methylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1 H-pyrazole-1-carboxamide (CAS 452099-05-7), N-tetrahydrofurfuryl-3-(2-chloro-6-fluoro-4-trifluoro-methylphenoxy)-5-methyl-1 H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon and 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);
preferably PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon and 2-chloro-3-methylsulfanyl-N-(1-methyltetrazol-5-yl)-4-(trifluoromethyl)benzamide (CAS 1361139-71-0);

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis Inhibitors:
compounds of group K1: dinitroanililnes such as benifluralin, butralin, dinitramine, ethaifluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthaldimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:
chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7', II.8 and II.9

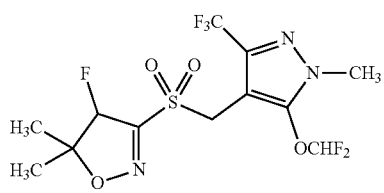

II.1

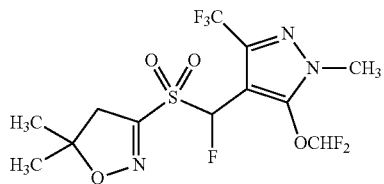

II.2

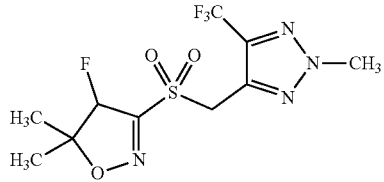

II.3

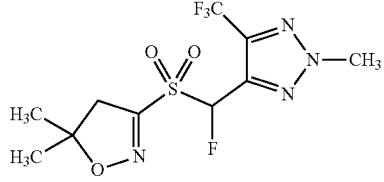

II.4

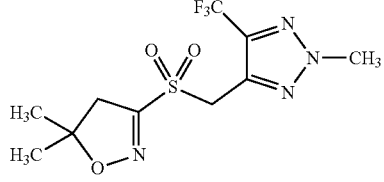

II.5

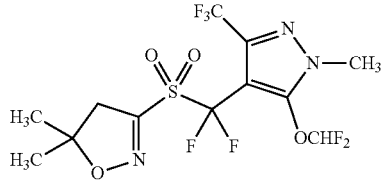

II.6

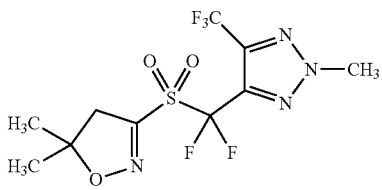

II.7

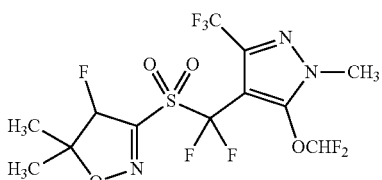

II.8

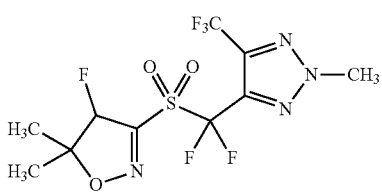

II.9 the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, isoxaben, triaziflam and 1-cyclohexyl-5-pentafluorphenyloxy-$1^4$-[1,2,4,6]thiatriazin-3-ylamine (CAS 175899-01-1);

b12) from the group of the decoupler herbicides:
dinoseb, dinoterb and DNOC and its salts;

b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Particularly preferred herbicides B are the herbicides B as defined above; in particular the herbicides B.1-B.86 listed below in table B:

TABLE B

| | Herbicide(s) B |
|---|---|
| B.1 | clethodim |
| B.2 | sethoxydim |
| B.3 | quizalofop |
| B.4 | fluazifop |
| B.5 | imazamox |
| B.6 | imazamox-ammonium |
| B.7 | imazaquin |
| B.8 | imazaquin-ammonium |
| B.9 | imazethapyr |
| B.10 | imazethapyr-ammonium |
| B.11 | imazethapyr-isopropylammonium |
| B.12 | cloransulam |
| B.13 | diclosulam |
| B.14 | flumetsulam |
| B.15 | chlorimuron |
| B.16 | pyrithiobac |
| B.17 | prosulfuron |
| B.18 | nicosulfuron |
| B.19 | primisulfuron |
| B.20 | foramsulfuron |
| B.21 | halosulfuron |
| B.22 | iodosulfuron |
| B.23 | trifloxysulfuron |
| B.24 | rimsulfuron |
| B.25 | thifensulfuron |
| B.26 | thifensulfuron-methyl |
| B.27 | ametryne |
| B.28 | atrazine |
| B.29 | bentazone |
| B.30 | bentazone-sodium |
| B.31 | bromoxynil |
| B.32 | bromoxynil-octanoate |
| B.33 | bromoxynil-heptanoate |
| B.34 | bromoxynil-potassium |
| B.35 | fluometuron |
| B.36 | simazin |
| B.37 | sulfentrazone |
| B.38 | carfentrazone-ethyl |
| B.39 | flumioxazin |
| B.40 | saflufenacil |
| B.41 | trifludimoxazin |
| B.42 | bicyclopyrone |
| B.43 | isoxaflutole |
| B.44 | mesotrione |
| B.45 | tembotrione |
| B.46 | topramezone |
| B.47 | topramezone-sodium |
| B.48 | glyphosate |
| B.49 | glyphosate-ammonium |
| B.50 | glyphosate-dimethylammonium |
| B.51 | glyphosate-isopropylammonium |
| B.52 | glyphosate-trimesium (sulfosate) |
| B.53 | glyphosate-potassium |
| B.54 | glufosinate |
| B.55 | glufosinate-ammonium |
| B.56 | glufosinate-P |
| B.57 | glufosinate-P-ammonium |
| B.58 | pendimethalin |
| B.59 | acetochlor |
| B.60 | flufenacet |
| B.61 | metolachlor |
| B.62 | S-metolachlor |
| B.63 | dimethenamid-P |
| B.64 | pyroxasulfone |
| B.65 | 2,4-D |

TABLE B-continued

| | Herbicide(s) B |
|---|---|
| B.66 | 2,4-D-isobutyl |
| B.67 | 2,4-D-dimethylammonium |
| B.68 | 2,4-D-N,N,N-trimethylethanolammonium |
| B.69 | dicamba |
| B.70 | dicamba-butotyl |
| B.71 | dicamba-diglycolamine |
| B.72 | dicamba-dimethylammonium |
| B.73 | dicamba-diolamine |
| B.74 | dicamba-isopropylammonium |
| B.75 | dicamba-potassium |
| B.76 | dicamba-sodium |
| B.77 | dicamba-trolamine |
| B.78 | dicamba-N,N-bis-(3-aminopropyl)methylamine |
| B.79 | dicamba-diethylenetriamine |
| B.80 | diflufenzopyr |
| B.81 | diflufenzopyr-sodium |
| B.82 | cinmethylin |
| B.83 | dicamba-diglycolamine + glyphosate-isopropylammonium |
| B.84 | dicamba-diglycolamine + glyphosate-potassium |
| B.85 | dicamba-N,N-bis-(3-aminopropyl)methylamine + glyphosate-isopropylammonium |
| B.86 | dicamba-N,N-bis-(3-aminopropyl)methylamine + glyphosate-potassium |

Particularly preferred herbicides B are selected from the group consisting of glyphosate, glyphosate-ammonium, glyphosate-dimethylammonium, glyphosate-isopropylammonium, glyphosate-trimesium (sulfosate), glyphosate-potassium, glufosinate, glufosinate-ammonium, glufosinate-P, glufosinate-P-ammonium, 2,4-D, 2,4-D-isobutyl, 2,4-D-dimethylammonium, 2,4-D-N,N,N-trimethylethanolammonium, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine and dicamba-diethylenetriamine.

Accordingly, in one embodiment of the invention, the method according to the present invention comprises the application of a herbicidal composition comprising at least one, preferably exactly one compound of formula (I), at least one further active compound selected from herbicides B, preferably herbicides B of class b1) to b15), and, in addition, a further active compound selected from the group consisting of glyphosate, glyphosate-ammonium, glyphosate-dimethyl-ammonium, glyphosate-isopropylammonium, glyphosate-trimesium (sulfosate), glyphosate-potassium, glufosinate, glufosinate-ammonium, glufosinate-P, glufosinate-P-ammonium, 2,4-D, 2,4-D-isobutyl, 2,4-D-dimethylammonium, 2,4-D-N,N,N-trimethylethanolammonium, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine and dicamba-diethylenetriamine to control PPO resistant weeds.

The present invention also relates to a method for controlling PPO resistant weeds in crops which comprises applying compositions, comprising at least one compound of formula (I) and at least one safener C.

Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or In the pre-emergence application or post-emergence application of the useful plant. The safeners and the compound of formula (I) and/or the herbicides B can be applied simultaneously or in succession.

Examples of preferred safeners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4), metcamifen, MG191 (2-dichloromethyl-2-methyl-1,3-dioxolane) or their salts and esters.

Especially preferred safeners are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4) and metcamifen or their salts and esters.

Particularly preferred safeners are benoxacor, cloquintocet, cyprosulfamide, dichlormid, fenchlorazole, fenclorim, furilazole, isoxadifen, mefenpyr, naphtalic anhydride, 4-(dichloro-acetyl)-1-oxa-4-azaspiro[4.5]decane (CAS 71526-07-3), 2,2,5-trimethyl-3-(dichloroacetyl)-1,3-oxazolidine (CAS 52836-31-4) and metcamifen or their salts and esters.

Particularly preferred safeners C, which, as component C, can be used in the method according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | metcamifen |

In another preferred embodiment of the Invention, the method according to the present invention comprises the application of a composition comprising, in addition to a compound of formula (I), at least one, especially exactly one safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660. The piperazine compounds of formula (III) as defined above (hereinafter also referred to as "compound III") as well as its pesticidal action and methods for preparation are described in WO 2010/049369, WO 2010/037727 und WO 2010/012649.

The assignment of the active compounds to the respective mechanisms of action is based on current knowledge. If several mechanisms of action apply to one active compound, this substance was only assigned to one mechanism of action.

Herbicide compounds B and safeners C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethyl-ammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecyl-ammonium, 2,4-D-tetradecylammonium, 2,4-D-triethylammonium, 2,4-D-tris(2-hydroxypro-pyl) ammonium, 2,4-D-tris(isopropyl)ammonium, 2,4-D-trolamine, 2,4-D-lithium, 2,4-D-sodium.

Examples of suitable esters of 2,4-D are 2,4-D-butotyl, 2,4-D-2-butoxypropyl, 2,4-D-3-butoxy-propyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-di-methylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethyl-ammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium and aminopyralid-tris(2-hydroxypropyl) ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

A suitable salt of bentazone is for example bentazone sodium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethyl-ammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

In one preferred embodiment of the invention, the method according to the present invention comprises the application of a composition comprising at least one, preferably exactly one, compound of formula (I) and at least one, preferably exactly one herbicide B.

In another preferred embodiment of the invention, the method according to the present invention comprises the application of a composition comprising at least one, preferably exactly one, compound of formula (I), and at least two, preferably exactly two herbicides B different from each other.

In another preferred embodiment of the invention, the method according to the present invention comprises the application of a composition comprising at least one, preferably exactly one, compound of formula (I), and at least three, preferably exactly three herbicides B different from each other.

According to a further preferred embodiment, the method according to the present invention comprises the application of a composition comprising ternary compositions which correspond to the binary compositions mentioned above and additionally comprise a safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3, active compounds of the formula (I) and either one or more, for example 1, 2 or 3, herbicides B or one or more safeners.

Correspondingly, the term "ternary compositions" includes compositions comprising one or more, for example 1, 2 or 3, active compounds of the formula (I), one or more, for example 1, 2 or 3, herbicides B and one or more, for example 1, 2 or 3, safeners C.

In another preferred embodiment, the method according to the present invention comprises the application of a composition comprising at least one, preferably exactly one compound of formula (I), and at least one, preferably exactly one safener C.

In another preferred embodiment, the method according to the present invention comprises the application of a composition comprising at least one, preferably exactly one compound of formula (I), at least one, preferably exactly one herbicide B, and at least one, preferably exactly one, safener C.

In another preferred embodiment, the method according to the present invention comprises the application of a composition comprising at least one, preferably exactly one compound of formula (I), preferably exactly two herbicides B different from each other, and at least one, preferably exactly one, safener C.

In another preferred embodiment, the method according to the present invention comprises the application of a composition comprising at least one, preferably exactly one compound of formula (I), at least three, preferably exactly three herbicides B different from each other, and at least one, preferably exactly one, safener C.

In binary compositions comprising at least one compound of formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The method according to the invention can be employed in a further number of crop plants for eliminating the PPO inhibitor herbicide resistant weeds. Examples of suitable crops are the following:

Allium cepa, Ananas comosus, Arachis hypogaea, Asparagus officinalis, Avena sativa, Beta vulgaris spec. altissima, Beta vulgaris spec. rapa, Brassica napus var. napus, Brassica napus var. napobrassica, Brassica rapa var. silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regla, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus lunatus, Phaseolus vulgaris, Picea abies, Pinus spec., Pistacia vera, Pisum sativum, Prunus avium, Prunus persica, Pyrus communis, Prunus armeniaca, Prunus cerasus, Prunus dulcis and prunus domestica, Ribes syivestre, Ricinus communis, Saccharum officinarum, Secale cereale, Sinapis alba, Solanum tuberosum, Sorghum bicolor (S. vulgare), Theobroma cacao, Trifolium pratense, Triticum aestivum, Triticale, Triticum durum, Vicia faba, Vitis vinifera, Zea mays.

Preferred crops are Arachis hypogaea, Beta vulgaris spec. altissima, Brassica napus var. napus, Brassica oleracea, Citrus limon, Citrus sinensis, Coffea arabica (Coffea canephora, Coffea liberica), Cynodon dactyion, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus spec., Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (S. vulgare), Triticale, Triticum aestivum, Triticum durum, Vicia faba, Vitis vinifera and Zea mays.

Especially preferred crops are crops of cereals, corn, soybeans, rice, oilseed rape/canola, sunflowers, cotton, potatoes, peanuts or plantation crops.

Particularly preferred are crops of corn, soybeans, oilseed rape/canola and cotton.

In another embodiment, the invention refers to a plant cell transformed by a nucleic acid encoding a herbicide tolerant PPO polypeptide disclosed herein or to a plant cell which has been mutated to obtain a plant expressing a nucleic acid encoding a mutated PPO polypeptide according to the present invention, wherein expression of the nucleic acid in the plant cell results in increased resistance or tolerance to PPO inhibitor herbicides, preferably the compounds of formula (I), as compared to a wild type variety of the plant cell.

The term "expression/expressing" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product To obtain the desired effect, i.e. plants that are tolerant or resistant to PPO inhibitor herbicides, preferably the compounds of formula (I) of the present invention, it will be understood that the at least one nucleic acid is "overexpressed" by methods and means known to the person skilled in the art.

The term "increased expression" or "overexpression" as used herein means any form of expression that is additional to the original wild-type expression level. Methods for Increasing expression of genes or gene products are well documented in the art and Include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994)

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to Introduce the gene of Interest into a suitable ancestor cell. The methods described for the transformation and regeneration of plants from plant tissues or plant cells may be utilized for transient or for stable transformation.

Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aidemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, ads. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for Instance using Southern analysis, for the presence of the gene of Interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the wild-type or mutated PPO nucleic acid comprises a polynucleotide sequence selected from the group consisting of: a) a polynucleotide encoding a polypeptide of interest; b) a polynucleotide comprising at least 60 consecutive nucleotides of any of a); and c) a polynucleotide complementary to the polynucleotide of any of a) through b).

Preferably, the expression of the nucleic acid in the plant results in the plant's increased resistance to PPO inhibitor herbicides, preferably the compounds of formula (I), as compared to a wild type variety of the plant.

In another embodiment, the invention refers to a plant, comprising a plant cell according to the present invention, wherein expression of the nucleic acid in the plant results in the plant's increased resistance to PPO inhibitor herbicides, preferably the compounds of formula (I), as compared to a wild type variety of the plant.

The plants described herein can be either transgenic crop plants or non-transgenic plants.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues in order to allow for the expression of the mutated PPO of the present invention. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein. Furthermore, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

Plants containing mutations arising due to non-spontaneous mutagenesis and selective breeding are referred to herein as non-transgenic plants and are included in the present invention. In embodiments wherein the plant is transgenic and comprises multiple mutated PPO nucleic acids, the nucleic acids can be derived from different genomes or from the same genome. Alternatively, in embodiments wherein the plant is non-transgenic and comprises multiple mutated PPO nucleic acids, the nucleic acids are located on different genomes or on the same genome. As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induce and/or selected by human action. Methods of inducing mutations can induce mutations in random positions in the genetic material or can induce mutations in specific locations in the genetic material (i.e., can be directed mutagenesis techniques), such as by use of a genoplasty technique.

In certain embodiments, the present invention involves herbicide-resistant plants that are produced by mutation breeding. Such plants comprise a polynucleotide encoding a mutated PPO and are tolerant to one or more PPO inhibitor herbicides, preferably compounds of formula (I). Such methods can involve, for example, exposing the plants or seeds to a mutagen, particularly a chemical mutagen such as, for example, ethyl methanesulfonate (EMS) and selecting for plants that have enhanced tolerance to at least one or more PPO inhibitor herbicides, preferably compounds of formula (I).

However, the present invention is not limited to herbicide-tolerant plants that are produced by a mutagenesis method involving the chemical mutagen EMS. Any mutagenesis method known in the art may be used to produce the herbicide-resistant plants of the present invention. Such mutagenesis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radio-isotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference In addition to the definition above, the term "plant" is intended to encompass crop plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, and the like.

The plant of the present invention comprises at least one mutated PPO nucleic acid or over-expressed wild-type PPO nucleic acid, and has increased tolerance to PPO inhibitor herbicides, preferably the compounds of formula (I), as compared to a wild-type variety of the plant. It is possible for the plants of the present invention to have multiple wild-type or mutated PPO nucleic acids from different genomes since these plants can contain more than one genome. For example, a plant contains two genomes, usually referred to as the A and B genomes. Because PPO is a required metabolic enzyme, it is assumed that each genome has at least one gene coding for the PPO enzyme (i.e. at least one PPO gene). As used herein, the term "PPO gene locus" refers to the position of an PPO gene on a genome, and the terms "PPO gene" and "PPO nucleic acid" refer to a nucleic acid encoding the PPO enzyme. The PPO nucleic acid on each genome differs in its nucleotide sequence from an PPO nucleic acid on another genome. One of skill in the art can determine the genome of origin of each PPO nucleic acid through genetic crossing and/or either sequencing methods or exonuclease digestion methods known to those of skill in the art.

The present invention includes plants comprising one, two, three, or more mutated PPO alleles, wherein the plant has increased tolerance to PPO inhibitor herbicides, preferably the compounds of formula (I), as compared to a wild-type variety of the plant. The mutated PPO alleles can comprise a nucleotide sequence selected from the group consisting of a polynucleotide encoding a polypeptide of interest, a polynucleotide comprising at least 60 consecutive nucleotides of any of the aforementioned polynucleotides; and a polynucleotide complementary to any of the aforementioned polynucleotides.

"Alleles" or "allelic variants" are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

The term "variety" refers to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. The terms "breeding line" or "line" refer to a group of plants within a cultivar defined by the sharing of a common set of characteristics or traits accepted by those skilled in the art as sufficient to distinguish one breeding line or line from another breeding line or line. There is no implication in either term that all plants of any given breeding line or line will be genetically identical at either the whole gene or molecular level or that any given plant will be homozygous at all loci. A breeding line or line is considered "true breeding" for a particular trait if, when the true-breeding line or breeding line is self-pollinated, all of the progeny contain the trait. In the present invention, the trait arises from a mutation in a PPO gene of the plant or seed.

In some embodiments, traditional plant breeding is employed whereby the PPO inhibitor herbicides-tolerant, preferably the compounds of formula (I)-tolerant, trait is introduced in the progeny plant resulting therefrom. In one embodiment, the present invention provides a method for producing a PPO inhibitor herbicide-tolerant, preferably a compound of formula (I)-tolerant, progeny plant, the method comprising: crossing a parent plant with a PPO inhibitor herbicide-tolerant, preferably a compound of formula (I)-tolerant, plant to introduce the PPO inhibitor herbicide-tolerance, preferably the compound of formula (I)-tolerance, characteristics of the PPO Inhibitor herbicide-tolerant, preferably the compound of formula (I)-tolerant, plant into the germplasm of the progeny plant, wherein the progeny plant has Increased tolerance to the PPO inhibitor herbicide, preferably the compound of formula (I), relative to the parent plant. In other embodiments, the method further comprises the step of introgressing the PPO inhibitor herbicide-tolerance, preferably the compound of formula (I)-tolerance, characteristics through traditional plant breeding techniques to obtain a descendent plant having the PPO inhibitor herbicide-tolerance, preferably the compound of formula (I)-tolerance, characteristics.

The herbicide-resistant plants of the invention that comprise polynucleotides encoding mutated PPO polypeptides also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the mutated PPO polypeptides of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In other aspects, plants of the invention include those plants which, in addition to being tolerant to PPO inhibitor herbicides, preferably the compounds of formula (I), have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, PPO inhibitor herbicides-tolerant, preferably compounds of formula (I)-tolerant, plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, PPO inhibitor herbicides, preferably compounds of formula (I)-tolerant, plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, PPO inhibitor herbicides-tolerant, preferably compounds of formula (I)-tolerant, plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype PPO proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicide-degrading activity.

PPO inhibitor herbicides-tolerant, preferably compounds of formula (I)-tolerant, plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, PPO inhibitor herbicides-tolerant, preferably compounds of formula (I)-tolerant, plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins;

proteinase Inhibitors, such as trypsin Inhibitors, serine protease Inhibitors, patatin, cystatin or papain Inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda).

In some embodiments, expression of one or more protein toxins (e.g., insecticidal proteins) in the PPO inhibitor herbicides-tolerant, preferably compounds of formula (I)-tolerant, plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes* bicolor); the grain beetle *Ahasverus advena*; the summer schafer *Amphimallon soistitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera,* and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricome*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegoblum paniceum*; the yellow mealworm beetle *Tenebrio molitor*, the flour beetles *Tribollum castaneum* and *Tribollum confusum*; warehouse and cabinet beetles {*Trogoderma* spp.); the sunflower beetle *Zygogramma exclamationis; Dermaptera* (earwigs) such as the European earwig *Forficula auricularia* and the striped earwig *Labidura riparia; Dictyoptera* such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); isoptera (termites) including species from the families Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypli*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear *psylla Cacopsylla pyricola*; the currant aphid *Cryptomyzus ribis*; the grape *Phylloxera Daktulosphaira vitifoliae*; the citrus psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae*; Lepidoptera such as *Adoxophyes orana* (summer fruit tortrix moth); *Archips podana* (fruit tree tortrix moth); *Bucculatrix pyrivorella* (pear leafminer); *Bucculatrix thurberiella* (cotton leaf perforator); *Bupalus piniarius* (pine looper); *Carpocapsa*

*pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); Heliothis vires cens (tobacco budworm), *Homeosoma electellum* (sunflower moth); *Homona magnanima* (oriental tea tree tortrix moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armyworm); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differ entialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria; Symphyla* such as the garden symphylan *Scutigerella immaculata*; Thysanoptera such as the tobacco thrips *Frankliniella fusca*, the flower *thrips Frankliniella intonsa*, the western flower *thrips Frankliniella* occidentalism the cotton bud *thrips Frankliniella schultzei*, the banded greenhouse *thrips Hercinothrips femoralis*, the soybean thrips *Neohydatothrips variabilis*, Kelly's citrus thrips *Pezothrips kellyanus*, the avocado thrips *Scirtothrlps perseae*, the melon thrips *Thrips palmi*, and the onion thrips *Thrips tabaci*; and the like, and combinations comprising one or more of the foregoing organisms.

In some embodiments, expression of one or more protein toxins (e.g., insecticidal proteins) in the PPO inhibitor herbicides-tolerant, preferably compounds of formula (I)-tolerant, plants is effective for controlling flea beetles, i.e. members of the flea beetle tribe of family Chrysomelidae, preferably against *Phyllotreta* spp., such as *Phyllotreta cruciferae* and/or *Phyllotreta triolata*. In other embodiments, expression of one or more protein toxins {e.g., insecticidal proteins) in the PPO inhibitor herbicides-tolerant, preferably compounds of formula (I)-tolerant, plants is effective for controlling cabbage seedpod weevil, the Bertha armyworm, *Lygus* bugs, or the diamondback moth.

Furthermore, in one embodiment, PPO inhibitor herbicides-tolerant, preferably compounds of formula (I)-tolerant, plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, PPO inhibitor herbicides-tolerant, preferably compounds of formula (I)-tolerant, plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, PPO inhibitor herbicides-tolerant, preferably compounds of formula (I)-tolerant, plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, PPO inhibitor herbicides-tolerant, preferably compounds of formula (I)-tolerant, plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, PPO inhibitor herbicides-tolerant, preferably compounds of formula (I)-tolerant, plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate(glucobrassicin), I-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2-trisinapoyl-gentiobiose, 1,2-diferuloylgentiobiose, 1,2'-disinapoyl-2-feruloylgentiobiose, 3-0-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, PPO inhibitor herbicides-tolerant, preferably compounds of formula (I)-tolerant, plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as camosol, rosmarinic acid, glycyrrhizin and saponins; chlorophyll; chlorphyllin, sugars, anthocyanins, and vanilla. In other embodiments, PPO inhibitor herbicides-tolerant, preferably compounds of formula (I)-tolerant, plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin ill, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

It is to be understood that the plant of the present invention can comprise a wild type PPO nucleic acid in addition to a mutated PPO nucleic acid. It is contemplated that the PPO inhibitor herbicides-tolerant, preferably compounds of formula (I)-tolerant, lines may contain a mutation in only one of multiple PPO isoenzymes. Therefore, the present invention includes a plant comprising one or more mutated PPO nucleic acids in addition to one or more wild type PPO nucleic acids.

Examples of PPO inhibitor herbicide resistant weed species are Asian copperleaf (*Acalypha australis*), smooth pigweed (*Amaranthus hybridus*), Palmer amaranth (*Amaranthus Palmeri*), redroot pigweed (*Amaranthus retroflexus*), tall/common waterhemp (*Amaranthus tuberculatus* or *Amaranthus rudis*), common ragweed (*Ambrosia artemisiifolia*), wild oat (*Avena fatua*), fleabane (*Conyza ambigua*), marestail (*Conyza Canadensis*), flixweed (*Descurainia Sophia*), wild poinsettia (*Euphorbia heterophylia*) and eastern groundsel (*Senecio vernalis*).

Preferred is the method according to the invention, wherein the PPO resistant weeds to be controlled are selected from the group consisting of Asian copperleaf, smooth pigweed, Palmer amaranth, redroot pigweed, tall/common waterhemp, common ragweed, wild oat, fleabane, marestall, flixweed, wild poinsettia and Eastern groundsel; preferably are selected from Asian copperleaf, smooth pigweed, Palmer amaranth, redroot pigweed, tall/common waterhemp, common ragweed, wild oat, flixweed, wild poinsettia and Eastern groundsel;
particularly preferably are selected from the group consisting of waterhemp, Palmer amaranth and common ragweed.

In a particularly preferred embodiment of the invention, the PPO resistant weed to be controlled is Asian copperleaf.

In another particularly preferred embodiment of the invention, the PPO resistant weed to be controlled is smooth pigweed.

In another particularly preferred embodiment of the invention, the PPO resistant weed to be controlled is Palmer amaranth.

In another particularly preferred embodiment of the invention, the PPO resistant weed to be controlled is redroot pigweed.

In another particularly preferred embodiment of the invention, the PPO resistant weed to be controlled is tall/common waterhemp.

In another particularly preferred embodiment of the invention, the PPO resistant weed to be controlled is common ragweed.

In another particularly preferred embodiment of the invention, the PPO resistant weed to be controlled is wild oat.

In a particularly preferred embodiment of the invention, the PPO resistant weed to be controlled is fleabane.

In a particularly preferred embodiment of the invention, the PPO resistant weed to be controlled is marestail.

In another particularly preferred embodiment of the invention, the PPO resistant weed to be controlled is flixweed.

In another particularly preferred embodiment of the invention, the PPO resistant weed to be controlled is wild poinsettia.

In another particularly preferred embodiment of the invention, the PPO resistant weed to be controlled is Eastern groundsel.

In another preferred embodiment of the invention the method according to the present invention comprises the application of a herbicidal composition comprising at least one, preferably exactly one compound (I) and at least one further active compound selected from herbicides B, preferably herbicides B of class b1) to b15), and safeners C (compound C) to PPO resistant weeds, such as Asian copperleaf, smooth pigweed, Palmer amaranth, redroot pigweed, tall/common waterhemp, common ragweed, wild oat, fleabane, marestail, flixweed, wild poinsettia and eastern groundsel.

In another preferred embodiment of the invention the method according to the present invention comprises the application of a herbicidal composition comprising at least one, preferably exactly one compound (I) and at least one further active compound selected from herbicides B, preferably herbicides B of class b1) to b15), and safeners C (compound C) to PPO resistant weeds, such as Asian copperleaf, smooth pigweed, Palmer amaranth, redroot pigweed, tall/common waterhemp, common ragweed, wild oat, flixweed, wild poinsettia and eastern groundsel.

In another preferred embodiment of the invention, the method according to the present invention comprises the application of a herbicidal composition comprising at least one, preferably exactly one compound (I) and at least one further active compound selected from herbicides B, preferably herbicides B of class b1) to b15), and safeners C (compound C) to PPO resistant weeds selected from common waterhemp, Palmer amaranth and common ragweed.

In a particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control Asian copperleaf.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control smooth pigweed.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control Palmer amaranth.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control redroot pigweed.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control tall/common waterhemp.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control common ragweed.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control wild oat.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control fleabane.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control marestail.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control flixweed.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control wild poinsettia.

In another particularly preferred embodiment of the invention, the method comprises the application of a herbicidal composition comprising at least one, preferably exactly one compound of formula (I) and at least one further active compound selected from herbicides B, preferably herbicides B of class b1) to b15), and safeners C (compound C) to control Eastern groundsel.

Particularly preferred are the methods 1.1 to 1.87, especially 1.1 to 1.82, wherein the substance(s) as defined in the respective row of table 1 is/are applied to Asian copperleaf:

TABLE 1

(methods 1.1 to 1.87)

| meth. no | cpd (I) | herbicide B |
|---|---|---|
| 1.1 | (I).1 | — |
| 1.2 | (I).1 | B.1 |
| 1.3 | (I).1 | B.2 |
| 1.4 | (I).1 | B.3 |
| 1.5 | (I).1 | B.4 |
| 1.6 | (I).1 | B.5 |
| 1.7 | (I).1 | B.6 |
| 1.8 | (I).1 | B.7 |
| 1.9 | (I).1 | B.8 |
| 1.10 | (I).1 | B.9 |
| 1.11 | (I).1 | B.10 |
| 1.12 | (I).1 | B.11 |
| 1.13 | (I).1 | B.12 |
| 1.14 | (I).1 | B.13 |
| 1.15 | (I).1 | B.14 |
| 1.16 | (I).1 | B.15 |
| 1.17 | (I).1 | B.16 |
| 1.18 | (I).1 | B.17 |
| 1.19 | (I).1 | B.18 |
| 1.20 | (I).1 | B.19 |
| 1.21 | (I).1 | B.20 |
| 1.22 | (I).1 | B.21 |
| 1.23 | (I).1 | B.22 |
| 1.24 | (I).1 | B.23 |
| 1.25 | (I).1 | B.24 |
| 1.26 | (I).1 | B.25 |
| 1.27 | (I).1 | B.26 |
| 1.28 | (I).1 | B.27 |
| 1.29 | (I).1 | B.28 |
| 1.30 | (I).1 | B.29 |
| 1.31 | (I).1 | B.30 |
| 1.32 | (I).1 | B.31 |
| 1.33 | (I).1 | B.32 |
| 1.34 | (I).1 | B.33 |
| 1.35 | (I).1 | B.34 |
| 1.36 | (I).1 | B.35 |
| 1.37 | (I).1 | B.36 |
| 1.38 | (I).1 | B.37 |
| 1.39 | (I).1 | B.38 |
| 1.40 | (I).1 | B.39 |
| 1.41 | (I).1 | B.40 |
| 1.42 | (I).1 | B.41 |
| 1.43 | (I).1 | B.42 |
| 1.44 | (I).1 | B.43 |
| 1.45 | (I).1 | B.44 |
| 1.46 | (I).1 | B.45 |
| 1.47 | (I).1 | B.46 |
| 1.48 | (I).1 | B.47 |
| 1.49 | (I).1 | B.48 |
| 1.50 | (I).1 | B.49 |
| 1.51 | (I).1 | B.50 |
| 1.52 | (I).1 | B.51 |
| 1.53 | (I).1 | B.52 |
| 1.54 | (I).1 | B.53 |
| 1.55 | (I).1 | B.54 |
| 1.56 | (I).1 | B.55 |
| 1.57 | (I).1 | B.56 |
| 1.58 | (I).1 | B.57 |
| 1.59 | (I).1 | B.58 |
| 1.60 | (I).1 | B.59 |
| 1.61 | (I).1 | B.60 |
| 1.62 | (I).1 | B.61 |
| 1.63 | (I).1 | B.62 |
| 1.64 | (I).1 | B.63 |
| 1.65 | (I).1 | B.64 |
| 1.66 | (I).1 | B.65 |
| 1.67 | (I).1 | B.66 |
| 1.68 | (I).1 | B.67 |
| 1.69 | (I).1 | B.68 |
| 1.70 | (I).1 | B.69 |
| 1.71 | (I).1 | B.70 |
| 1.72 | (I).1 | B.71 |
| 1.73 | (I).1 | B.72 |
| 1.74 | (I).1 | B.73 |
| 1.75 | (I).1 | B.74 |
| 1.76 | (I).1 | B.75 |
| 1.77 | (I).1 | B.76 |
| 1.78 | (I).1 | B.77 |
| 1.79 | (I).1 | B.78 |
| 1.80 | (I).1 | B.79 |
| 1.81 | (I).1 | B.80 |
| 1.82 | (I).1 | B.81 |
| 1.83 | (I).1 | B.82 |
| 1.84 | (I).1 | B.83 |
| 1.85 | (I).1 | B.84 |
| 1.86 | (I).1 | B.85 |
| 1.87 | (I).1 | B.86 |

The specific number for each single method is deductible as follows:

Method 1.20 for example comprises the application of the compound (I).1 and foramsulfuron (B.20) (see above as well as table B, entry B.20) to Asian copperleaf.

Method 2.20 for example comprises the application of the compound (I).1 and foramsulfuron (B.20) (see above as well as table B, entry B.20) to smooth pigweed.

Also especially preferred are the methods 2.1. to 2.87 which differ from the corresponding methods 1.1 to 1.87 only in that the substance(s) as defined in the respective row of table 1 is/are applied to smooth pigweed.

Also especially preferred are the methods 3.1. to 3.87 which differ from the corresponding methods 1.1 to 1.87 only in that the substance(s) as defined in the respective row of table 1 is/are applied to Palmer amaranth.

Also especially preferred are the methods 4.1. to 4.87 which differ from the corresponding methods 1.1 to 1.87 only in that the substance(s) as defined in the respective row of table 1 is/are applied to redroot pigweed.

Also especially preferred are the methods 5.1. to 5.87 which differ from the corresponding methods 1.1 to 1.87 only in that the substance(s) as defined in the respective row of table 1 is/are applied to tall/common waterhemp.

Also especially preferred are the methods 6.1. to 6.87 which differ from the corresponding methods 1.1 to 1.87 only in that the substance(s) as defined in the respective row of table 1 is/are applied to common ragweed.

Also especially preferred are the methods 7.1. to 7.87 which differ from the corresponding methods 1.1 to 1.87 only in that the substance(s) as defined in the respective row of table 1 is/are applied to wild oat Also especially preferred are the methods 8.1. to 8.87 which differ from the corresponding methods 1.1 to 1.87 only in that the substance(s) as defined in the respective row of table 1 is/are applied to fleabane.

Also especially preferred are the methods 9.1. to 9.87 which differ from the corresponding methods 1.1 to 1.87 only in that the substance(s) as defined in the respective row of table 1 is/are applied to marestail.

Also especially preferred are the methods 10.1. to 10.87 which differ from the corresponding methods 1.1 to 1.87 only in that the substance(s) as defined in the respective row of table 1 is/are applied to flixweed.

Also especially preferred are the methods 11.1. to 11.87 which differ from the corresponding methods 1.1 to 1.87 only in that the substance(s) as defined in the respective row of table 1 is/are applied to wild poinsettia.

Also especially preferred are the methods 12.1. to 12.87 which differ from the corresponding methods 1.1 to 1.87 only in that the substance(s) as defined in the respective row of table 1 is/are applied to eastern groundsel.

Also especially preferred are the methods 13.1. to 13.87 which differ from the corresponding methods 1.1 to 1.87 only in that within the substance(s) as defined in the respective row of table 1, compound (I).1 is replaced by compound (I).2.

Also especially preferred are the methods 14.1. to 14.87 which differ from the corresponding methods 1.1 to 1.87 only in that within the substance(s) as defined in the respective row of table 1, compound (I).1 is replaced by compound (I).2, and such defined substance(s) is/are applied to smooth pigweed.

Also especially preferred are the methods 15.1. to 15.87 which differ from the corresponding methods 1.1 to 1.87 only in that within the substance(s) as defined in the respective row of table 1, compound (I).1 is replaced by compound (I).2, and such defined substance(s) is/are applied to Palmer amaranth.

Also especially preferred are the methods 16.1. to 16.87 which differ from the corresponding methods 1.1 to 1.87 only in that within the substance(s) as defined in the respective row of table 1, compound (I).1 is replaced by compound (I).2, and such defined substance(s) is/are applied to redroot pigweed.

Also especially preferred are the methods 17.1. to 17.87 which differ from the corresponding methods 1.1 to 1.87 only in that within the substance(s) as defined in the respective row of table 1, compound (I).1 is replaced by compound (I).2, and such defined substance(s) is/are applied to tall/common waterhemp.

Also especially preferred are the methods 18.1. to 18.87 which differ from the corresponding methods 1.1 to 1.87 only in that within the substance(s) as defined in the respective row of table 1, compound (I).1 is replaced by compound (I).2, and such defined substance(s) is/are applied to common ragweed.

Also especially preferred are the methods 19.1. to 19.87 which differ from the corresponding methods 1.1 to 1.87 only in that within the substance(s) as defined in the respective row of table 1, compound (I).1 is replaced by compound (I).2, and such defined substance(s) is/are applied to wild oat.

Also especially preferred are the methods 20.1. to 20.87 which differ from the corresponding methods 1.1 to 1.87 only in that within the substance(s) as defined in the respective row of table 1, compound (I).1 is replaced by compound (I).2, and such defined substance(s) is/are applied to fleabane.

Also especially preferred are the methods 21.1. to 21.87 which differ from the corresponding methods 1.1 to 1.87 only in that within the substance(s) as defined in the respective row of table 1, compound (I).1 is replaced by compound (I).2, and such defined substance(s) is/are applied to marestail.

Also especially preferred are the methods 22.1. to 22.87 which differ from the corresponding methods 1.1 to 1.87 only in that within the substance(s) as defined in the respective row of table 1, compound (I).1 is replaced by compound (I).2, and such defined substance(s) is/are applied to flixweed.

Also especially preferred are the methods 23.1. to 23.87 which differ from the corresponding methods 1.1 to 1.87 only in that within the substance(s) as defined in the respective row of table 1, compound (I).1 is replaced by compound (I).2, and such defined substance(s) is/are applied to wild poinsettia.

Also especially preferred are the methods 24.1. to 24.87 which differ from the corresponding methods 1.1 to 1.87 only in that within the substance(s) as defined in the respective row of table 1, compound (I).1 is replaced by compound (I).2, and such defined substance(s) is/are applied to eastern groundsel.

Also especially preferred are the methods 25.1. to 25.87 which differ from the corresponding methods 1.1 to 1.87 only in that within the substance(s) as defined in the respective row of table 1, compound (I).1 is replaced by compound (I).3.

Also especially preferred are the methods 26.1. to 26.87 which differ from the corresponding methods 1.1 to 1.87 only in that within the substance(s) as defined in the respective row of table 1, compound (I).1 is replaced by compound (I).3, and such defined substance(s) is/are applied to smooth pigweed.

Also especially preferred are the methods 27.1. to 27.87 which differ from the corresponding methods 1.1 to 1.87 only in that within the substance(s) as defined in the respective row of table 1, compound (I).1 is replaced by compound (I).3, and such defined substance(s) is/are applied to Palmer amaranth.

Also especially preferred are the methods 28.1. to 28.87 which differ from the corresponding methods 1.1 to 1.87 only in that within the substance(s) as defined in the respective row of table 1, compound (I).1 is replaced by compound (I).3, and such defined substance(s) is/are applied to redroot pigweed.

Also especially preferred are the methods 29.1. to 29.87 which differ from the corresponding methods 1.1 to 1.87 only in that within the substance(s) as defined in the respective row of table 1, compound (I).1 is replaced by compound (I).3, and such defined substance(s) is/are applied to tall/common waterhemp.

Also especially preferred are the methods 30.1. to 30.87 which differ from the corresponding methods 1.1 to 1.87 only in that within the substance(s) as defined in the respective row of table 1, compound (I).1 is replaced by compound (I).3, and such defined substance(s) is/are applied to common ragweed.

Also especially preferred are the methods 31.1. to 31.87 which differ from the corresponding methods 1.1 to 1.87 only in that within the substance(s) as defined in the respective row of table 1, compound (I).1 is replaced by compound (I).3, and such defined substance(s) is/are applied to wild oat.

Also especially preferred are the methods 32.1. to 32.87 which differ from the corresponding methods 1.1 to 1.87 only in that within the substance(s) as defined in the respective row of table 1, compound (I).1 is replaced by compound (I).3, and such defined substance(s) is/are applied to fleabane.

Also especially preferred are the methods 33.1. to 33.87 which differ from the corresponding methods 1.1 to 1.87 only in that within the substance(s) as defined in the respective row of table 1, compound (I).1 is replaced by compound (I).3, and such defined substance(s) is/are applied to marestail.

Also especially preferred are the methods 34.1. to 34.87 which differ from the corresponding methods 1.1 to 1.87 only in that within the substance(s) as defined in the respective row of table 1, compound (I).1 is replaced by compound (I).3, and such defined substance(s) is/are applied to flixweed.

Also especially preferred are the methods 35.1. to 35.87 which differ from the corresponding methods 1.1 to 1.87 only in that within the substance(s) as defined in the respective row of table 1, compound (I).1 is replaced by compound (I).3, and such defined substance(s) is/are applied to wild poinsettia.

Also especially preferred are the methods 36.1. to 36.87 which differ from the corresponding methods 1.1 to 1.87 only in that within the substance(s) as defined in the respective row of table 1, compound (I).1 is replaced by compound (I).3, and such defined substance(s) is/are applied to eastern groundsel.

Also especially preferred are the methods 37.1. to 37.87 which differ from the corresponding methods 1.1 to 1.87 only in that within the substance(s) as defined in the respective row of table 1, compound (I).1 is replaced by compound (I).4.

Also especially preferred are the methods 38.1. to 38.87 which differ from the corresponding methods 1.1 to 1.87 only in that within the substance(s) as defined in the respective row of table 1, compound (I).1 is replaced by compound (I).4, and such defined substance(s) is/are applied to smooth pigweed.

Also especially preferred are the methods 39.1. to 39.87 which differ from the corresponding methods 1.1 to 1.87 only in that within the substance(s) as defined in the respective row of table 1, compound (I).1 is replaced by compound (I).4, and such defined substance(s) is/are applied to Palmer amaranth.

Also especially preferred are the methods 40.1. to 40.87 which differ from the corresponding methods 1.1 to 1.87 only in that within the substance(s) as defined in the respective row of table 1, compound (I).1 is replaced by compound (I).4, and such defined substance(s) is/are applied to redroot pigweed.

Also especially preferred are the methods 41.1. to 41.87 which differ from the corresponding methods 1.1 to 1.87 only in that within the substance(s) as defined in the respective row of table 1, compound (I).1 is replaced by compound (I).4, and such defined substance(s) is/are applied to tall/common waterhemp.

Also especially preferred are the methods 42.1. to 42.87 which differ from the corresponding methods 1.1 to 1.87 only in that within the substance(s) as defined in the respective row of table 1, compound (I).1 is replaced by compound (I).4, and such defined substance(s) is/are applied to common ragweed.

Also especially preferred are the methods 43.1. to 43.87 which differ from the corresponding methods 1.1 to 1.87 only in that within the substance(s) as defined in the respective row of table 1, compound (I).1 is replaced by compound (I).4, and such defined substance(s) is/are applied to wild oat.

Also especially preferred are the methods 44.1. to 44.87 which differ from the corresponding methods 1.1 to 1.87 only in that within the substance(s) as defined in the respective row of table 1, compound (I).1 is replaced by compound (I).4, and such defined substance(s) is/are applied to fleabane.

Also especially preferred are the methods 45.1. to 45.87 which differ from the corresponding methods 1.1 to 1.87 only in that within the substance(s) as defined in the respective row of table 1, compound (I).1 is replaced by compound (I).4, and such defined substance(s) is/are applied to marestail.

Also especially preferred are the methods 46.1. to 46.87 which differ from the corresponding methods 1.1 to 1.87 only in that within the substance(s) as defined in the respective row of table 1, compound (I).1 is replaced by compound (I).4, and such defined substance(s) is/are applied to flixweed.

Also especially preferred are the methods 47.1. to 47.87 which differ from the corresponding methods 1.1 to 1.87 only in that within the substance(s) as defined in the respective row of table 1, compound (I).1 is replaced by compound (I).4, and such defined substance(s) is/are applied to wild poinsettia.

Also especially preferred are the methods 48.1. to 48.87 which differ from the corresponding methods 1.1 to 1.87 only in that within the substance(s) as defined in the respective row of table 1, compound (I).1 is replaced by compound (I).4, and such defined substance(s) is/are applied to eastern groundsel.

Also especially preferred are the methods 49.1. to 49.87 which differ from the corresponding methods 1.1 to 1.87 only in that within the substance(s) as defined in the respective row of table 1, compound (I).1 is replaced by compound (I).5.

Also especially preferred are the methods 50.1. to 50.87 which differ from the corresponding methods 1.1 to 1.87 only in that within the substance(s) as defined in the respective row of table 1, compound (I).1 is replaced by compound (I).5, and such defined substance(s) is/are applied to smooth pigweed.

Also especially preferred are the methods 51.1. to 51.87 which differ from the corresponding methods 1.1 to 1.87 only in that within the substance(s) as defined in the respective row of table 1, compound (I).1 is replaced by compound (I).5, and such defined substance(s) is/are applied to Palmer amaranth.

Also especially preferred are the methods 52.1. to 52.87 which differ from the corresponding methods 1.1 to 1.87 only in that within the substance(s) as defined in the respective row of table 1, compound (I).1 is replaced by compound (I).5, and such defined substance(s) is/are applied to redroot pigweed.

Also especially preferred are the methods 53.1. to 53.87 which differ from the corresponding methods 1.1 to 1.87 only in that within the substance(s) as defined in the respective row of table 1, compound (I).1 is replaced by compound (I).5, and such defined substance(s) is/are applied to tall/common waterhemp.

Also especially preferred are the methods 54.1. to 54.87 which differ from the corresponding methods 1.1 to 1.87 only in that within the substance(s) as defined in the respective row of table 1, compound (I).1 is replaced by compound (I).5, and such defined substance(s) is/are applied to common ragweed.

Also especially preferred are the methods 55.1. to 55.87 which differ from the corresponding methods 1.1 to 1.87 only in that within the substance(s) as defined in the respective row of table 1, compound (I).1 is replaced by compound (I).5, and such defined substance(s) is/are applied to wild oat.

Also especially preferred are the methods 56.1. to 56.87 which differ from the corresponding methods 1.1 to 1.87 only in that within the substance(s) as defined in the respective row of table 1, compound (I).1 is replaced by compound (I).5, and such defined substance(s) is/are applied to fleabane.

Also especially preferred are the methods 57.1. to 57.87 which differ from the corresponding methods 1.1 to 1.87 only in that within the substance(s) as defined in the respective row of table 1, compound (I).1 is replaced by compound (I).5, and such defined substance(s) is/are applied to marestail.

Also especially preferred are the methods 58.1. to 58.87 which differ from the corresponding methods 1.1 to 1.87 only in that within the substance(s) as defined in the respective row of table 1, compound (I).1 is replaced by compound (I).5, and such defined substance(s) is/are applied to flixweed.

Also especially preferred are the methods 59.1. to 59.87 which differ from the corresponding methods 1.1 to 1.87 only in that within the substance(s) as defined in the respective row of table 1, compound (I).1 is replaced by compound (I).5, and such defined substance(s) is/are applied to wild poinsettia.

Also especially preferred are the methods 60.1. to 60.87 which differ from the corresponding methods 1.1 to 1.87 only in that within the substance(s) as defined in the respective row of table 1, compound (I).1 is replaced by compound (I).5, and such defined substance(s) is/are applied to eastern groundsel.

Also especially preferred are the methods 61.1. to 61.87 which differ from the corresponding methods 1.1 to 1.87 only in that within the substance(s) as defined in the respective row of table 1, compound (I).1 is replaced by compound (I).6.

Also especially preferred are the methods 62.1. to 62.87 which differ from the corresponding methods 1.1 to 1.87 only in that within the substance(s) as defined in the respective row of table 1, compound (I).1 is replaced by compound (I).6, and such defined substance(s) is/are applied to smooth pigweed.

Also especially preferred are the methods 63.1. to 63.87 which differ from the corresponding methods 1.1 to 1.87 only in that within the substance(s) as defined in the respective row of table 1, compound (I).1 is replaced by compound (I).6, and such defined substance(s) is/are applied to Palmer amaranth.

Also especially preferred are the methods 64.1. to 64.87 which differ from the corresponding methods 1.1 to 1.87 only in that within the substance(s) as defined in the respective row of table 1, compound (I).1 is replaced by compound (I).6, and such defined substance(s) is/are applied to redroot pigweed.

Also especially preferred are the methods 65.1. to 65.87 which differ from the corresponding methods 1.1 to 1.87 only in that within the substance(s) as defined in the respective row of table 1, compound (I).1 is replaced by compound (I).6, and such defined substance(s) is/are applied to tall/common waterhemp.

Also especially preferred are the methods 66.1. to 66.87 which differ from the corresponding methods 1.1 to 1.87 only in that within the substance(s) as defined in the respective row of table 1, compound (I).1 is replaced by compound (I).6, and such defined substance(s) is/are applied to common ragweed.

Also especially preferred are the methods 67.1. to 67.87 which differ from the corresponding methods 1.1 to 1.87 only in that within the substance(s) as defined in the respective row of table 1, compound (I).1 is replaced by compound (I).6, and such defined substance(s) is/are applied to wild oat.

Also especially preferred are the methods 68.1. to 68.87 which differ from the corresponding methods 1.1 to 1.87 only in that within the substance(s) as defined in the respective row of table 1, compound (I).1 is replaced by compound (I).6, and such defined substance(s) is/are applied to fleabane.

Also especially preferred are the methods 69.1. to 69.87 which differ from the corresponding methods 1.1 to 1.87 only in that within the substance(s) as defined in the respective row of table 1, compound (I).1 is replaced by compound (I).6, and such defined substance(s) is/are applied to marestail.

Also especially preferred are the methods 70.1. to 70.87 which differ from the corresponding methods 1.1 to 1.87 only in that within the substance(s) as defined in the respective row of table 1, compound (I).1 is replaced by compound (I).6, and such defined substance(s) is/are applied to flixweed.

Also especially preferred are the methods 71.1. to 71.87 which differ from the corresponding methods 1.1 to 1.87 only in that within the substance(s) as defined in the respective row of table 1, compound (I).1 is replaced by compound (I).6, and such defined substance(s) is/are applied to wild poinsettia.

Also especially preferred are the methods 72.1. to 72.87 which differ from the corresponding methods 1.1 to 1.87 only in that within the substance(s) as defined in the respective row of table 1, compound (I).1 is replaced by compound (I).6, and such defined substance(s) is/are applied to eastern groundsel.

The agrochemical compositions which can be used for the method according to the Invention comprise an herbicidal effective amount of at least one compound of formula (I), optionally at least one further active compound selected from herbicides B and safeners C, and auxiliaries which are customary for the formulation of crop protection agents.

The compounds of formula (I), or herbicidal compositions comprising the compounds of formula (I), can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol®23 (Rhone Poulenc) or Veegum® (from R. T. Vanderbilt), and also organic and inorganic sheet minerals, such as Attaclay® (from Engelhard).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol. Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers.

Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkylated seed oil, alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylaryisulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or concomitant grinding the active Ingredients together with a solid carrier.

Granules, for example coated granules, Impregnated granules and homogeneous granules, can be prepared by binding the active Ingredients to solid carriers.

Aqueous use forms can be prepared from emulsion concentrates, suspensions, pastes, wettable powders or water-dispersible granules by adding water.

To prepare emulsions, pastes or oil dispersions, the compounds of formula (I), or herbicidal compositions comprising the compounds of formula (I), either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the active compounds, especially of the compounds of formula (I), or herbicidal compositions comprising the compounds of formula (I), in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the compounds of formula (I) according to the present invention the active ingredients, e.g. the compounds of formula (I), or herbicidal compositions comprising the compounds of formula (I), are present in suspended, emulsified or dissolved form. The formulation according to the invention can be in the form of aqueous solutions, powders, suspensions, also highly concentrated aqueous, oily or other suspensions or dispersions, aqueous emulsions, aqueous microemulsions, aqueous suspo-emulsions, oil dispersions, pastes, dusts, materials for spreading or granules.

The compounds of formula (I) according to the present invention, or herbicidal compositions comprising the compounds of formula (I), can, for example, be formulated as follows:

1. Products for dilution with water
A) Water-soluble concentrates
10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight
B) Dispersible concentrates
20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.
C) Emulsifiable concentrates
15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.
D) Emulsions
25 parts by weight of active compound are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.
E) Suspensions
In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.
F) Water-dispersible granules and water-soluble granules
50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.
G) Water-dispersible powders and water-soluble powders
75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.
H) Gel formulations
In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.
2. Products to be applied undiluted
I) Dusts
5 parts by weight of active compound are ground finely and mixed intimately with 95 parts by weight of finely divided kaolin. This gives a dusting powder with an active compound content of 5% by weight.
J) Granules (GR, FG, GG, MG)
0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.
K) ULV solutions (UL)
10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

Application can be done before, during and/or after, preferably during and/or after, the emergence of the PPO resistant weeds.

The compounds of formula (I) or the herbicidal compositions comprising them can be applied pre- or post-emergence, pre-plant or together with the seed of a crop plant. It is also possible to apply the method by applying seed pretreated with the compound of formula (I), or herbicidal compositions comprising them, of a crop plant.

If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the method, i.e. the compounds of formula (I) or the herbicidal compositions comprising them, can be applied by treating plant propagation material, particularly seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the compounds of formula (I) according to the invention or the compositions prepared therefrom. Here, the herbicidal compositions can be applied diluted or undiluted.

The term "seed" comprises plant reproductive material of all types, such as, for example, corms, grains, seeds, fruits, tubers, bulbs, nuts, seedlings and similar forms. Here, preferably, the term seed describes grains and seeds. The seed used can be seed of the useful plants mentioned above, but also the seed of transgenic plants or plants obtained by customary breeding methods.

The compound of formula (I) or composition comprising the compound of formula (I) according to the present invention may be applied prior to planting, at planting, after planting and prior to emergence of, and over the top of or as a directed spray to or near crops, preferably herbicide resistant crops, to control PPO herbicide resistant weeds near the crops without injury to the crops. If the compounds of formula (I) or composition comprising the compound of formula (I) according to the present invention are applied prior to planting of a crop, they may preferably be applied to control not only PPO resistant weeds but any vegetation Including weeds (such as PPO resistant weeds), volunteer crop plants and other vegetation (so-called 'burn-down' application).

The compound of formula (I) or composition comprising the compound of formula (I) according to the present invention may furthermore be applied to non-crop areas such as e. g. Industrial sites, railroads, powerlines or the vicinity thereof, as well as for forestry uses.

The rates of application of the active compound of formula (I) according to the present invention (total amount of compound of formula (I)) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the compounds of formula (I) are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the compounds of formula (I) is 0.1 to 1000 g/ha, preferably to 750 g/ha, more preferably 5 to 500 g/ha, of active substance.

To treat the seed, the compounds I are generally employed in amounts of from 0.001 to 10 kg per 100 kg of seed.

Examples: —The herbicidal activity of the compound of formula (I) was demonstrated by the following experiments:

The culture containers used were plastic flowerpots containing loamy sand with approximately 3.0% of humus as the substrate. The seeds of the test plants were sown separately for each species and/or resistant biotype. For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted.

This cover caused uniform germination of the test plants, unless this had been impaired by the active ingredients. For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment. Depending on the species, the plants were kept at 10-25° C. or 20-35° C., respectively. The test period extended over 2 to 4 weeks. During this time, the plants were tended, and their response to the Individual treatments was evaluated.

The evaluation was carried out by using a scale from 0 to 100. 100 means no emergence of the plants or complete destruction of at least the above-ground parts, and 0 means no damage, or normal course of growth.

The plants used in a first greenhouse experiment were of the following species and biotype (*Ambrosia eliator* mentioned below is to be understood being a variety of *Ambrosia artemisilfolia*):

| Weed no. | Bayer code | Scientific name | Common name | Biotype |
|---|---|---|---|---|
| w.1 | AMATA | *Amaranthus tamariscinus* | Common waterhemp | Sensitive |
| w.2 | AMATA | *Amaranthus tamariscinus* | Common waterhemp | PPO resistant biotype 1 |
| w.3 | AMATA | *Amaranthus tamariscinus* | Common waterhemp | PPO resistant biotype 2 |
| w.4 | AMBEL | *Ambrosia elatior* | Common ragweed | Sensitive |
| w.5 | AMBEL | *Ambrosia elatior* | Common ragweed | PPO resistant biotype 3 that contains the R98L mutation |
| w.6 | AMBEL | *Ambrosia elatior* | Common ragweed | PPO resistant biotype 4 that contains the R98L mutation |

The results shown in the following table 2 demonstrate that compound (I).1 has very good activity on both sensitive (w.1, w.4) and resistant weeds (w.2, w.3, w.5, w.6) whereas the known PPO inhibitor flumioxazin shows much weaker control of resistant in comparison to sensitive biotypes.

TABLE 2

| Herbicide compound | Use rate [g/ha] | Weed control (%) | | | | | |
|---|---|---|---|---|---|---|---|
| | | w.1 | w.2 | w.3 | w.4 | w.5 | w.6 |
| (I).1 | 2 | 100 | 100 | 100 | 100 | 100 | 100 |
| (I).1 | 1 | 100 | 100 | 100 | 100 | 100 | 100 |
| flumioxazin | 2 | 95 | 30 | 70 | 65 | 10 | 20 |
| flumioxazin | 1 | 90 | 30 | 0 | 50 | 0 | 0 |

In another greenhouse experiment, plants of the following species and biotype were tested:

| Weed no. | Bayer code | Scientific name | Common name | Biotype |
|---|---|---|---|---|
| w.7 | AMATU | *Amaranthus tuberculatus* | Tall waterhemp | Sensitive |

-continued

| Weed no. | Bayer code | Scientific name | Common name | Biotype |
|---|---|---|---|---|
| w.8 | AMATU | Amaranthus tuberculatus | Tall waterhemp | PPO resistant biotype 5 that contains the AG210 mutation |
| w.9 | AMATU | Amaranthus tuberculatus | Tall waterhemp | PPO resistant biotype 6 that does not contain the AG210 mutation |

The results shown in the following table 3 demonstrate that compound (I).1 has very good activity on both sensitive (w.7) and resistant weeds contain the ΔG210 mutation (w.8) as well as those that don't (w.9).

TABLE 3

| Herbicide compound | Use rate [g/ha] | Weed control (%) | | |
|---|---|---|---|---|
| | | 7 | 8 | 9 |
| (I).1 | 2 | 100 | 100 | 100 |
| (I).1 | 1 | 100 | 100 | 95 |

The plants used in a third greenhouse experiment were of the following species and biotype:

| Weed no. | Bayer code | Scientific name | Common name | Biotype |
|---|---|---|---|---|
| w.10 | AMATA | Amaranthus tamariscinus | Common waterhemp | Sensitive |
| w.11 | AMATA | Amaranthus tamariscinus | Common waterhemp | PPO resistant biotype 7 |
| w.12 | AMATA | Amaranthus tamariscinus | Common waterhemp | PPO resistant biotype 8 |

The results shown in the following table 4 demonstrate that compound (I).4 has very good activity on both sensitive (w.10) and resistant weeds (w.11, w.12) whereas the known PPO inhibitor azafenidin shows much weaker control of resistant in comparison to sensitive biotypes.

TABLE 4

| Herbicide compound | Use rate [g/ha] | Weed control (%) | | |
|---|---|---|---|---|
| | | w.10 | w.11 | w.12 |
| (I).4 | 4 | 100 | 100 | 99 |
| (I).4 | 2 | 100 | 89 | 100 |
| azafenidin | 4 | 98 | 73 | 72 |
| azafenidin | 2 | 95 | 67 | 70 |

The invention claimed is:

1. A compound of formula (I):

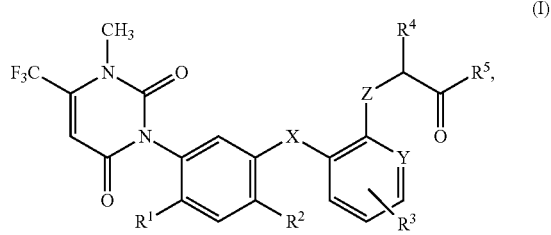

wherein:
$R^1$ is Cl;
$R^2$ is Cl;
$R^3$ is H;
$R^4$ is H;
$R^5$ is $OR^8$, where $R^8$ is $C_1$-$C_6$-alkyl;
X is O;
Y is N; and
Z is O.

2. The compound of claim 1, wherein $R^8$ is $C_2H_5$.

3. A herbicidal composition comprising: a compound of formula (I) according to claim 1; and a herbicide selected from the group consisting of classes b1) to b15):
  b1) lipid biosynthesis inhibitors;
  b2) acetolactate synthase inhibitors (ALS inhibitors);
  b3) photosynthesis inhibitors;
  b4) protoporphyrinogen-IX oxidase inhibitors (PPO inhibitors) other than the compounds of formula (I);
  b5) bleacher herbicides;
  b6) enolpyruvyl shikimate 3-phosphate synthase inhibitors (EPSP inhibitors);
  b7) glutamine synthetase inhibitors;
  b8) 7,8-dihydropteroate synthase inhibitors (DHP inhibitors);
  b9) mitosis inhibitors;
  b10) inhibitors of the synthesis of very long chain fatty acids (VLCFA inhibitors);
  b11) cellulose biosynthesis inhibitors;
  b12) decoupler herbicides;
  b13) auxinic herbicides;
  b14) auxin transport inhibitors; and
  b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters; including their agriculturally acceptable salts or derivatives.

4. The herbicidal composition of claim 3, wherein $R^8$ is $C_2H_5$ in the compound of formula (I).

* * * * *